US009540658B2

(12) United States Patent
Mizuguchi et al.

(10) Patent No.: US 9,540,658 B2
(45) Date of Patent: Jan. 10, 2017

(54) ADENOVIRUS VECTOR

(75) Inventors: Hiroyuki Mizuguchi, Osaka (JP); Takao Hayakawa, Tokyo (JP); Fuminori Sakurai, Hyogo (JP)

(73) Assignees: Fuso Pharmaceutical Industries, Ltd., Osaka (JP); Hiroyuki Mizuguchi, Osaka (JP); Takao Hayakawa, Tokyo (JP); Fuminori Sakurai, Hyogo (JP)

( * ) Notice: Subject to any disclaimer, the term of this patent is extended or adjusted under 35 U.S.C. 154(b) by 1853 days.

(21) Appl. No.: 10/516,504

(22) PCT Filed: Jun. 5, 2003

(86) PCT No.: PCT/JP03/07146
§ 371 (c)(1),
(2), (4) Date: Dec. 2, 2004

(87) PCT Pub. No.: WO03/104469
PCT Pub. Date: Dec. 18, 2003

(65) Prior Publication Data
US 2005/0176129 A1    Aug. 11, 2005

(30) Foreign Application Priority Data
Jun. 5, 2002   (JP) ................................ 2002-164015

(51) Int. Cl.
*C12N 15/861* (2006.01)
*A61K 48/00* (2006.01)
*A61K 31/713* (2006.01)
*C12N 15/86* (2006.01)

(52) U.S. Cl.
CPC ........... *C12N 15/86* (2013.01); *C12N 2510/00* (2013.01); *C12N 2710/10343* (2013.01)

(58) Field of Classification Search
None
See application file for complete search history.

(56) References Cited

U.S. PATENT DOCUMENTS

| 5,880,102 | A | 3/1999 | George et al. | |
|---|---|---|---|---|
| 6,492,169 | B1* | 12/2002 | Vogels et al. | 435/325 |
| 2001/0033833 | A1* | 10/2001 | Schraa et al. | 424/93.2 |
| 2003/0185801 | A1* | 10/2003 | Vogels et al. | 424/93.2 |
| 2004/0106194 | A1* | 6/2004 | Bett et al. | 435/320.1 |
| 2004/0136958 | A1* | 7/2004 | Wadell et al. | 424/93.2 |

FOREIGN PATENT DOCUMENTS

| CA | 2 289 611 A1 | 5/1998 |
|---|---|---|
| WO | WO-98/53087 A1 | 11/1998 |
| WO | WO 02/40665 A | 5/2002 |

OTHER PUBLICATIONS

Gao et al, Human adenovirus type 35: nucleotide sequence and vector development, Gene Therapy (2003) 10, 1941-1949.*
Havenga et al, Novel replication-incompetent adenoviral B-group vectors: high vector stability and yield in PER.C6 cells, Journal of General Virology (2006), 87, 2135-2143.*
C.F. Basler et al., "Sequence of the immunoregulatory early region 3 and flanking sequences of adenovirus type 35", Gene, vol. 170, No. 2, May 8, 1996, pp. 249-254.
V. Krougliak et al., "Development of Cell Lines Capable of Complementing E1, E4, and Protein IX Defective Adenovirus Type 5 Mutants", Human Gene Therapy, vol. 6, No. 12, Dec. 1, 1995, pp. 1575-1586.
D.M. Shayakhmetov et al., "Efficient Gene Transfer Into Human CD34+ Cells by a Retargeted Adenovirus Vector", Journal of Virology, vol. 74, No. 6, Mar. 2003, pp. 2567-2583.
B.C. Trapnell, "Adenoivral Vectors for Gene Transfer" Advanced Drug Delivery Reviews, vol. 12, 1993, pp. 185-199.
P R Flomenberg et al., "Sequence and Genetic Organization of Adenovirus Type 35 early region 3", Journal of Virology, vol. 62, No. 11, Nov. 1988, pp. 4431-4437.
Gen-Qi Liu et al., "A Thermolabile Mutant of Adenovirus 5 Resulting from a Substitution Mutation in the Protein VIII Gene", Journal of Virology, Mar. 1985, vol. 53, No. 3, pp. 920-925.
Daniel R. Gallie et al., "Visualization mRNA Expression in Plant Protoplasts: Factors Influencing Efficient mRNA Uptake and Translation", The Plant Cell, vol. 1, pp. 301-311, 1989.
Bett et al., "Packaging Capacity and Stability of Human Adenovirus Type 5 Vectors". Journal of Virology, Oct. 1993, pp. 5911-5921.

* cited by examiner

Primary Examiner — Maria Marvich
(74) Attorney, Agent, or Firm — Foley & Lardner LLP

(57) ABSTRACT

This invention relates to an adenovirus vector having excellent gene transfection activity on specific cell lines, particularly on hematopoietic cells. This adenovirus vector derives from the adenovirus type 35 genome by at least partial or total deletion of the E1 region therefrom. The adenovirus vector according to this invention has excellent gene transfection activity on specific cell lines, particularly on hematopoietic cells, ES cells, pluripotent stem cells, blood stem cells, and tissue stem cells.

5 Claims, 5 Drawing Sheets

SEQUENCE LISTING

<160> NUMBER OF SEQ ID NOS: 1

<210> SEQ ID NO 1
<211> LENGTH: 34794
<212> TYPE: DNA
<213> ORGANISM: Adenovirus type 35

<400> SEQUENCE: 1

| | | | | | |
|---|---|---|---|---|---|
| catcatcaat | aatataccttt | atagatggaa | tggtgccaat | atgtaaatga | ggtgatttta | 60 |
| aaaagtgtgg | gccgtgtggt | gattggctgt | ggggttaacg | gttaaaaggg | gcggcgcggc | 120 |
| cgtgggaaaa | tgacgtttta | tgggggtgga | gttttttttgc | aagttgtcgc | gggaaatgtt | 180 |
| acgcataaaa | aggcttcttt | tctcacggaa | ctacttagtt | ttcccacggt | atttaacagg | 240 |
| aaatgaggta | gttttgaccg | gatgcaagtg | aaaattgctg | attttcgcgc | gaaaactgaa | 300 |
| tgaggaagtg | ttttttctgaa | taatgtggta | tttatggcag | ggtggagtat | ttgttcaggg | 360 |
| ccaggtagac | tttgacccat | tacgtggagg | tttcgattac | cgtgtttttt | acctgaattt | 420 |
| ccgcgtaccg | tgtcaaagtc | ttctgttttt | acgtaggtgt | cagctgatcg | ctagggtatt | 480 |
| tatacctcag | ggtttgtgtc | aagaggccac | tcttgagtgc | cagcgagaag | agttttctcc | 540 |
| tctgcgccgg | cagtttaata | ataaaaaaat | gagagatttg | cgatttctgc | ctcaggaaat | 600 |
| aatctctgct | gagactggaa | atgaaatatt | ggagcttgtg | gtgcacgccc | tgatgggaga | 660 |
| cgatccggag | ccacctgtgc | agcttttttga | gcctcctacg | cttcaggaac | tgtatgattt | 720 |
| agaggtagag | ggatcggagg | attctaatga | ggaagctgtg | aatggctttt | ttaccgattc | 780 |
| tatgctttta | gctgctaatg | aaggattaga | attagatccg | cctttggaca | ctttcaatac | 840 |
| tccaggggtg | attgtggaaa | gcggtacagg | tgtaagaaaa | ttacctgatt | tgagttccgt | 900 |
| ggactgtgat | ttgcactgct | atgaagacgg | gttttcctccg | agtgatgagg | aggaccatga | 960 |
| aaaggagcag | tccatgcaga | ctgcagcggg | tgagggagtg | aaggctgcca | atgttggttt | 1020 |
| tcagttggat | tgcccggagc | ttcctggaca | tggctgtaag | tcttgtgaat | tcacaggaa | 1080 |
| aaatactgga | gtaaaggaac | tgttatgttc | gctttgttat | atgagaacgc | actgccactt | 1140 |
| tatttacagt | aagtgtgttt | aagttaaaat | ttaaaggaat | atgctgtttt | tcacatgtat | 1200 |
| attgagtgtg | agttttgtgc | ttcttattat | aggtcctgtg | tctgatgctg | atgaatcacc | 1260 |
| atctcctgat | tctactacct | cacctcctga | tattcaagca | cctgttcctg | tggacgtgcg | 1320 |
| caagcccatt | cctgtgaagc | ttaagcctgg | gaaacgtcca | gcagtggaga | aacttgagga | 1380 |
| cttgttacag | ggtggggacg | gaccttttgga | cttgagtaca | cggaaacgtc | caagacaata | 1440 |
| agtgttccat | atccgtgttt | acttaaggtg | acgtcaatat | ttgtgtgaga | gtgcaatgta | 1500 |
| ataaaaatat | gttaactgtt | cactggtttt | tattgctttt | tgggcgggga | ctcaggtata | 1560 |
| taagtagaag | cagacctgtg | tggttagctc | ataggagctg | gctttcatcc | atggaggttt | 1620 |
| gggccatttt | ggaagacctt | aggaagacta | ggcaactgtt | agagagcgct | tcggacggag | 1680 |
| tctccggttt | ttggagattc | tggttcgcta | gtgaattagc | tagggtagtt | tttaggataa | 1740 |
| aacaggacta | taaacaagaa | tttgaaaagt | tgttggtaga | ttgcccagga | cttttttgaag | 1800 |
| ctccttaattt | gggccatcag | gttcacttta | aagaaaaagt | tttatcagtt | ttagactttt | 1860 |
| caacccccagg | tagaactgct | gctgctgtgg | cttttcttac | tttttatatta | gataaatgga | 1920 |
| tcccgcagac | tcatttcagc | aggggatacg | ttttggattt | catagccaca | gcattgtgga | 1980 |
| gaacatggaa | ggttcgcaag | atgaggacaa | tcttaggtta | ctggccagtg | cagcctttgg | 2040 |
| gtgtagcggg | aatcctgagg | catccaccgg | tcatgccagc | ggttctggag | gaggaacagc | 2100 |

```
aagaggacaa cccgagagcc ggcctggacc ctccagtgga ggaggcggag tagctgactt    2160
gtctcctgaa ctgcaacggg tgcttactgg atctacgtcc actggacggg atagggcgt    2220 taagagggag agggcatcca gtggtactga tgctagatct gagttggctt taagtttaat    2280
gagtcgcaga cgtcctgaaa ccatttggtg gcatgaggtt cagaaagagg gaagggatga    2340
agtttctgta ttgcaggaga aatattcact ggaacaggtg aaaacatgtt ggttggagcc    2400
agaggatgat tgggcggtgg ccattaaaaa ttatgccaag atagctttga ggcctgataa    2460
acagtataag atcagtagac ggattaatat ccggaatgct tgttacatat ctggaaatgg    2520
ggctgaggtg gtaatagata ctcaagacaa gacagttatt agatgctgca tgatggatat    2580
gtggcctgga gtagtcggta tggaagcagt cacttttgta aatgttaagt ttaggggaga    2640
tggttataat ggaatagtgt ttatggccaa taccaaactt atattgcatg ttgtagctt     2700 ttttggtttc aacaatacct gtgtagatgc ctggggacag gttagtgtac gggggtgtag    2760
tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tctttgacat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggga catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc accctttggac   3660 gcagctgcag ccgctgccgc cgcctctgtc gccgctaaca ctgtgcttgg aatgggttac    3720
tatggaagca tcgtggctaa ttccacttcc tctaataacc cttctacact gactcaggac    3780
aagttacttg tcccttttggc ccagctggag gctttgaccc aacgtctggg tgaacttttct   3840 cagcaggtgg ccgagttgcg agtacaaact gagtctgctg tcggcacggc aaagtctaaa    3900
taaaaaaaat tccagaatca atgaataaat aaacgagctt gttgttgatt taaaatcaag    3960
tgtttttatt tcattttcg cgcacggtat gccctggacc accgatctcg atcattgaga     4020
actcggtgga ttttttccag aatcctatag aggtgggatt gaatgtttag atacatgggc    4080
attaggccgt ctttggggtg gagatagctc cattgaaggg attcatgctc cggggtagtg    4140
ttgtaaatca cccagtcata acaaggtcgc agtgcatggt gttgcacaat atctttttaga   4200 agtaggctga ttgccacaga taagcccttg gtgtaggtgt ttacaaaccg gttgagctgg    4260
gaggggtgca ttcgaggtga aattatgtgc attttggatt ggattttttaa gttggcaata   4320 ttgccgccaa gatcccgtct tgggttcatg ttatgaagga ctaccaagac ggtgtatccg    4380
gtacatttag gaaattttatc gtgcagcttg gatgaaaag cgtggaaaaa tttgagacca    4440
cccttgtgtc ctccgagatt ttccatgcac tcatccatga taatagcaat ggggccgtgg    4500
```

```
gcagcggcgc gggcaaacac gttccgtggg tctgacacat catagttatg ttcctgagtt   4560
aaatcatcat aagccatttt aatgaatttg gggcggagcg taccagattg gggtatgaat   4620
gttccttcgg gccccggagc atagttcccc tcacagattt gcatttccca agctttcagt   4680
tctgagggtg gaatcatgtc cacctggggg gctatgaaga acaccgtttc gggggcgggg   4740
gtgattagtt gggatgatag caagtttctg agcaattgag atttgccaca tccggtgggg   4800
ccataaataa ttccgattac aggttgcagg tggtagttta gggaacggca actgccgtct   4860
tctcgaagca aggggggccac ctcgttcatc atttccctta catgcatatt ttcccgcacc   4920
aaatccatta ggaggcgctc tcctcctagt gatagaagtt cttgtagtga ggaaaagttt   4980
ttcagcggtt ttagaccgtc agccatgggc attttggaaa gagtttgctg caaaagttct   5040
agtctgttcc acagttcagt gatgtgttct atggcatctc gatccagcag acctcctcgt   5100
ttcgcgggtt tggacggctc ctggagtagg gtatgagacg atgggcgtcc agcgctgcca   5160
gggttcggtc cttccagggt ctcagtgttc gagtcagggt tgtttccgtc acagtgaagg   5220
ggtgtgcgcc tgcttgggcg cttgccaggg tgcgcttcag actcattctg ctggtggaga   5280
acttctgtcg cttggcgccc tgtatgtcgg ccaagtagca gtttaccatg agttcgtagt   5340
tgagcgcctc ggctgcgtgg cctttggcgc ggagcttacc tttggaagtt ttcttgcata   5400
ccgggcagta taggcatttc agcgcataca gcttgggcgc aaggaaaatg gattctgggg   5460
agtatgcatc cgcgccgcag gaggcgcaaa cagtttcaca ttccaccagc caggttaaat   5520
ccggttcatt ggggtcaaaa acaagttttc cgccatattt tttgatgcgt ttcttacctt   5580
tggtctccat aagttcgtgt cctcgttgag tgacaaacag gctgtccgta tctccgtaga   5640
ctgattttac aggcctcttc tccagtggag tgcctcggtc ttcttcgtac aggaactctg   5700
accactctga tacaaaggcg cgcgtccagg ccagcacaaa ggaggctatg tgggaggggt   5760
agcgatcgtt gtcaaccagg gggtccacct tttccaaagt atgcaaacac atgtcaccct   5820
cttcaacatc caggaatgtg attggcttgt aggtgtattt cacgtgacct ggggtccccg   5880 ctggggggggt ataaaagggg gcggttcttt gctcttcctc actgtcttcc ggatcgctgt   5940
ccaggaacgt cagctgttgg ggtaggtatt ccctctcgaa ggcgggcatg acctctgcac   6000
tcaggttgtc agtttctaag aacgaggagg atttgatatt gacagtgccg gttgagatgc   6060 cttttcatgag gttttcgtcc atttggtcag aaaacacaat ttttttattg tcaagtttgg   6120
tggcaaatga tccatacagg gcgttggata aaagtttggc aatggatcgc atggtttggt   6180
tcttttcctt gtccgcgcgc tctttggcgg cgatgttgag ttggacatac tcgcgtgcca   6240
ggcacttcca ttcggggaag atagttgtta attcatctgg cacgattctc acttgccacc   6300
ctcgattatg caaggtaatt aaatccacac tggtggccac ctcgcctcga aggggttcat   6360
tggtccaaca gagcctacct cctttcctag aacagaaagg gggaagtggg tctagcataa   6420
gttcatcggg agggtctgca tccatggtaa agattcccgg aagtaaatcc ttatcaaaat   6480
agctgatggg agtggggtca tctaaggcca tttgccattc tcgagctgcc agtgcgcgct   6540
catatgggtt aaggggactg ccccagggca tgggatgggt gagagcagag gcatacatgc   6600
cacagatgtc atagacgtag atgggatcct caaagatgcc tatgtaggtt ggatagcatc   6660 gccccccctct gatacttgct cgcacatagt catatagttc atgtgatggc gctagcagcc   6720
ccggacccaa gttggtgcga ttgggttttt ctgttctgta gacgatctgg cgaaagatgg   6780
cgtgagaatt ggaagagatg gtgggtcttt gaaaatgtt gaaatgggca tgaggtagac   6840
ctacagagtc tctgacaaag tgggcataag attcttgaag cttggttacc agttcggcgg   6900
```

```
tgacaagtac gtctagggcg cagtagtcaa gtgtttcttg aatgatgtca taacctggtt      6960
ggtttttctt ttcccacagt tcgcggttga gaaggtattc ttcgcgatcc ttccagtact      7020
cttctagcgg aaacccgtct ttgtctgcac ggtaagatcc tagcatgtag aactgattaa      7080
ctgccttgta agggcagcag cccttctcta cgggtagaga gtatgcttga gcagcttttc      7140
gtagcgaagc gtgagtaagg gcaaaggtgt ctctgaccat gactttgaga aattggtatt      7200
tgaagtccat gtcgtcacag gctccctgtt cccagagttg gaagtctacc cgtttcttgt      7260
aggcggggtt gggcaaagcg aaagtaacat cattgaagag aatcttaccg gctctgggca      7320
taaaattgcg agtgatgcgg aaaggctgtg gtacttccgc tcgattgttg atcacctggg      7380
cagctaggac gatttcgtcg aaaccgttga tgttgtgtcc tacgatgtat aattctatga      7440
aacgcggcgt gcctctgacg tgaggtagct tactgagctc atcaaaggtt aggtctgtgg      7500
ggtcagataa ggcgtagtgt tcgagagccc attcgtgcag gtgaggattt gcatgtagga      7560
atgatgacca agatctacc gccagtgctg tttgtaactg gtcccgatac tgacgaaaat      7620
gccggccaat tgccatttt tctggagtga cacagtagaa ggtctggggg tcttgttgcc      7680
atcgatccca cttgagttta atggctagat cgtgggccat gttgacgaga cgctcttctc      7740
ctgagagttt catgaccagc atgaaaggaa ctagttgttt gccaaaggat cccatccagg      7800
tgtaagtttc cacatcgtag gtcaggaaga gtctttctgt gcgaggatga gagccgatcg      7860
ggaagaactg gatttcctgc caccagttgg aggattggct gttgatgtga tggaagtaga      7920
agtttctgcg gcgcgccgag cattcgtgtt tgtgcttgta cagacggccg cagtagtcgc      7980
agcgttgcac gggttgtatc tcgtgaatga gctgtacctg gcttcccttg acgagaaatt      8040
tcagtgggaa gccgaggcct ggcgattgta tctcgtgctc ttctatattc gctgtatcgg      8100
cctgttcatc ttctgtttcg atggtggtca tgctgacgag ccccgcggg aggcaagtcc      8160
agacctcggc gcgggagggg cggagctgaa ggacgagagc gcgcaggctg gagctgtcca      8220
gagtcctgag acgctgcgga ctcaggttag taggtaggga cagaagatta acttgcatga      8280
tcttttccag ggcgtgcggg aggttcagat ggtacttgat ttccacaggt tcgtttgtag      8340
agacgtcaat ggcttgcagg gttccgtgtc ctttgggcgc cactaccgta cctttgtttt      8400
ttcttttgat cggtggtggc tctcttgctt cttgcatgct cagaagcggt gacggggacg      8460
cgcgccgggc ggcagcggtt gttccggacc cgggggcatg gctggtagtg gcacgtcggc      8520
gccgcgcacg ggcaggttct ggtattgcgc tctgagaaga cttgcgtgcg ccaccacgcg      8580
tcgattgacg tcttgtatct gacgtctctg ggtgaaagct accggccccg tgagcttgaa      8640
cctgaaagag agttcaacag aatcaatttc ggtatcgtta acggcagctt gtctcagtat      8700
ttcttgtacg tcaccagagt tgtcctggta ggcgatctcc gccatgaact gctcgatttc      8760
ttcctcctga agatctccgc gacccgctct ttcgacggtg gccgcgaggt cattggagat      8820
acggcccatg agttgggaga atgcattcat gcccgcctcg ttccagacgc ggctgtaaac      8880
cacggccccc tcggagtctc ttgcgcgcat caccacctga gcgaggttaa gctccacgtg      8940
tctggtgaag accgcatagt tgcataggcg ctgaaaaagg tagttgagtg tggtggcaat      9000
gtgttcggca acgaagaaat acatgatcca tcgtctcagc ggcatttcgc taacatcgcc      9060
cagagcttcc aagcgctcca tggcctcgta gaagtccacg gcaaaattaa aaaactggga      9120
gtttcgcgcg gacacggtca attcctcctc gagaagacgg atgagttcgg ctatggtggc      9180
ccgtacttcg cgttcgaagg ctcccgggat ctcttcttcc tcttctatct cttcttccac      9240
taacatctct tcttcgtctt caggcggggg cggagggggc acgcggcgac gtcgacggcg      9300
```

-continued

```
cacgggcaaa cggtcgatga atcgttcaat gacctctccg cggcggcggc gcatggtttc    9360
agtgacggcg cggccgttct cgcgcggtcg cagagtaaaa acaccgccgc gcatctcctt    9420
aaagtggtga ctgggaggtt ctccgtttgg gagggagagg gcgctgatta tacattttat    9480
taattggccc gtagggactg cgcgcagaga tctgatcgtg tcaagatcca cgggatctga    9540
aaacctttcg acgaaagcgt ctaaccagtc acagtcacaa ggtaggctga gtacggcttc    9600
ttgtgggcgg gggtggttat gtgttcggtc tgggtcttct gtttcttctt catctcggga    9660
aggtgagacg atgctgctgg tgatgaaatt aaagtaggca gttctaagac ggcggatggt    9720
ggcgaggagc accaggtctt tgggtccggc ttgctggata cgcaggcgat tggccattcc    9780
ccaagcatta tcctgacatc tagcaagatc tttgtagtag tcttgcatga gccgttctac    9840
gggcacttct tcctcacccg ttctgccatg catacgtgtg agtccaaatc cgcgcattgg    9900
ttgtaccagt gccaagtcag ctacgactct ttcggcgagg atggcttgct gtacttgggt    9960
aagggtggct tgaaagtcat caaaatccac aaagcggtgg taagcccctg tattaatggt   10020
gtaagcacag ttggccatga ctgaccagtt aactgtctgg tgaccagggc gcacgagctc   10080
ggtgtattta aggcgcgaat aggcgcgggt gtcaaagatg taatcgttgc aggtgcgcac   10140
cagatactgg tacactataa gaaaatgcgg cggtggttgg cggtagagag gccatcgttc   10200
tgtagctgga gcgccagggg cgaggtcttc aacataagg cggtgatagc cgtagatgta    10260
cctggacatc caggtgattc ctgcggcggt agtagaagcc cgaggaaact cgcgtacgcg   10320
gttccaaatg ttgcgtagcg gcatgaagta gttcattgta ggcacggttt gaccagtgag   10380
gcgcgcgcag tcattgatgc tctatagaca cggagaaaat gaaagcgttc agcgactcga   10440
ctccgtagcc tggaggaacg tgaacgggtt gggtcgcggt gtaccccggt cgagacttg    10500
tactcgagcc ggccggagcc gcggctaacg tggtattggc actcccgtct cgacccagcc   10560
tacaaaaatc caggatacgg aatcgagtcg ttttgctggt ttccgaatgg cagggaagtg   10620
agtcctattt ttttttttt tttgccgctc agatgcatcc cgtgctgcga cagatgcgcc   10680
cccaacaaca gccccctcg cagcagcagc agcagcaacc acaaaaggct gtccctgcaa    10740
ctactgcaac tgccgccgtg agcggtgcgg gacagcccgc ctatgatctg gacttggaag   10800
agggcgaagg actggcacgt ctaggtgcgc cttcgcccga gcggcatccg cgagttcaac   10860
tgaaaaaaga ttctcgcgag gcgtatgtgc cccaacagaa cctatttaga gacagaagcg   10920
gcgaggagcc ggaggagatg cgagcttccc gctttaacgc gggtcgtgag ctgcgtcacg   10980
gtttggaccg aagacgagtg ttgcgagacg aggatttcga agttgatgaa gtgacaggga   11040
tcagtcctgc cagggcacac gtggctgcag ccaaccttgt atcggcttac gagcagacag   11100
taaaggaaga gcgtaacttc caaaagtctt ttaataatca tgtgcgaacc ctgattgccc   11160
gcgaagaagt taccctggt ttgatgcatt tgtgggattt gatggaagct atcattcaga    11220
accctactag caaacctctg accgcccagc tgtttctggt ggtgcaacac agcagagaca   11280
atgaggcttt cagagaggcg ctgctgaaca tcaccgaacc cgaggggaga tggttgtatg   11340
atcttatcaa cattctacag agtatcatag tgcaggagcg gagcctgggc ctggccgaga   11400
aggtagctgc catcaattac tcggttttga gcttgggaaa atattacgct cgcaaaatct   11460
acaagactcc atacgttccc atagacaagg aggtgaagat agatgggttc tacatgcgca   11520
tgacgctcaa ggtcttgacc ctgagcgatg atcttgggt gtatcgcaat gacagaatgc    11580
atcgcgcggt tagcgccagc aggaggcgcg agttaagcga cagggaactg atgcacagtt   11640
tgcaaagagc tctgactgga gctggaaccg agggtgagaa ttacttcgac atgggagctg   11700
```

```
acttgcagtg gcagcctagt cgcagggctc tgagcgccgc gacggcagga tgtgagcttc    11760
cttacataga agaggcggat gaaggcgagg aggaagaggg cgagtacttg gaagactgat    11820
ggcacaaccc gtgtttttg ctagatggaa cagcaagcac cggatcccgc aatgcgggcg     11880
gcgctgcaga gccagccgtc cggcattaac tcctcgacg attggaccca ggccatgcaa     11940
cgtatcatgg cgttgacgac tcgcaacccc gaagccttta gacagcaacc ccaggccaac    12000
cgtctatcgg ccatcatgga agctgtagtg ccttcccgat ctaatcccac tcatgagaag    12060
gtcctggcca tcgtgaacgc gttggtggag aacaaagcta ttcgtccaga tgaggccgga    12120
ctggtataca acgctctctt agaacgcgtg gctcgctaca acagtagcaa tgtgcaaacc    12180
aatttggacc gtatgataac agatgtacgc gaagccgtgt ctcagcgcga aaggttccag    12240
cgtgatgcca acctgggttc gctggtggcg ttaaatgctt tcttgagtac tcagcctgct    12300
aatgtgccgc gtggtcaaca ggattatact aacttttaa gtgctttgag actgatggta     12360
tcagaagtac ctcagagcga agtgtatcag tccggtcctg attacttctt tcagactagc    12420
agacagggct tgcagacggt aaatctgagc caagctttta aaaaccttaa aggtttgtgg    12480
ggagtgcatg ccccggtagg agaaagagca accgtgtcta gcttgttaac tccgaactcc    12540
cgcctgttat tactgttggt agctccttc accgacagcg gtagcatcga ccgtaattcc     12600
tatttgggtt acctactaaa cctgtatcgc gaagccatag ggcaaagtca ggtggacgag    12660
cagacctatc aagaaattac ccaagtcagt cgcgcttggg gacaggaaga cactggcagt    12720
ttggaagcca ctctgaactt cttgcttacc aatcggtctc aaaagatccc tcctcaatat    12780
gctcttactg cggaggagga gaggatcctt agatatgtgc agcagagcgt gggattgttt    12840
ctgatgcaag aggggcaac tccgactgca gcactggaca tgacagcgcg aaatatggag     12900
cccagcatgt atgccagtaa ccgacctttc attaacaaac tgctggacta cttgcacaga    12960
gctgccgcta tgaactctga ttatttcacc aatgccatct taaacccgca ctggctgccc    13020
ccacctggtt tctacacggg cgaatatgac atgcccgacc ctaatgacgg atttctgtgg    13080
gacgacgtgg acagcgatgt tttttcacct ctttctgatc atcgcacgtg gaaaaaggaa    13140
ggcggtgata gaatgcattc ttctgcatcg ctgtccgggg tcatgggtgc taccgcggct    13200
gagcccgagt ctgcaagtcc ttttcctagt ctacccttt ctctacacag tgtacgtagc     13260
agcgaagtgg gtagaataag tcgcccgagt ttaatgggcg aagaggagta cctaaacgat    13320
tccttgctca gaccggcaag agaaaaaaat ttcccaaaca atggaataga agtttggtg     13380 gataaaatga gtagatggaa gactatgct caggatcaca gagacgagcc tgggatcatg     13440
gggactacaa gtagagcgag ccgtagacgc cagcgccatg acagacagag gggtcttgtg    13500
tgggacgatg aggattcggc cgatgatagc agcgtgttgg acttgggtgg gagaggaagg    13560
ggcaacccgt ttgctcattt gcgccctcgc ttgggtggta tgttgtgaaa aaaaataaaa    13620
aagaaaaact caccaaggcc atggcgacga gcgtacgttc gttcttcttt attatctgtg    13680
tctagtataa tgaggcgagt cgtgctaggc ggagcggtgt tgtatccgga gggtcctcct    13740
ccttcgtacg agagcgtgat gcagcagcag caggcgacgg cggtgatgca atccccactg    13800
gaggctccct ttgtgcctcc gcgatacctg gcacctacgg agggcagaaa cagcattcgt    13860
tactcggaac tggcacctca gtacgatacc accaggttgt atctggtgga caacaagtcg    13920
gcggacattg cttctctgaa ctatcagaat gaccacagca acttcttgac cacggtggtg    13980
cagaacaatg actttacccc tacggaagcc agcacccaga ccattaactt tgatgaacga    14040
tcgcggtggg gcggtcagct aaagaccatc atgcatacta acatgccaaa cgtgaacgag    14100
```

```
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa cttttcagtt actatgacta ttgatttgat gaacaatgcc   14280
atcatagata attacttgaa agtgggtaga cagaatggag tgcttgaaag tgacattggt   14340
gttaagttcg acaccaggaa cttcaagctg ggatgggatc ccgaaaccaa gttgatcatg   14400
cctggagtgt atacgtatga agccttccat cctgacattg tcttactgcc tggctgcgga   14460
gtggatttta ccgagagtcg tttgagcaac cttcttggta tcagaaaaaa acagccattt   14520
caagagggtt ttaagatttt gtatgaagat ttagaaggtg gtaatattcc ggccctcttg   14580
gatgtagatg cctatgagaa cagtaagaaa gaacaaaaag ccaaaataga agctgctaca   14640
gctgctgcag aagctaaggc aaacatagtt gccagcgact ctacaagggt tgctaacgct   14700
ggagaggtca gaggagacaa ttttgcgcca acacctgttc cgactgcaga atcattattg   14760
gccgatgtgt ctgaaggaac ggacgtgaaa ctcactattc aacctgtaga aaaagatagt   14820
aagaatagaa gctataatgt gttggaagac aaaatcaaca cagcctatcg cagttggtat   14880
ctttcgtaca attatggcga tcccgaaaaa ggagtgcgtt cctggacatt gctcaccacc   14940
tcagatgtca cctgcggagc agagcaggtt tactggtcgc ttccagacat gatgaaggat   15000
cctgtcactt tccgctccac tagacaagtc agtaactacc ctgtggtggg tgcagagctt   15060
atgcccgtct tctcaaagag cttctacaac gaacaagctg tgtactccca gcagctccgc   15120
cagtccacct cgcttacgca cgtcttcaac cgctttcctg agaaccagat tttaatccgt   15180
ccgccggcgc ccaccattac caccgtcagt gaaaacgttc ctgctctcac agatcacggg   15240
accctgccgt tgcgcagcag tatccgggga gtccaacgtg tgaccgttac tgacgccaga   15300
cgccgcacct gtccctacgt gtacaaggca ctgggcatag tcgcaccgcg cgtcctttca   15360
agccgcactt tctaaaaaaa aaaaatgtcc attcttatct cgcccagtaa taacaccggt   15420
tggggtctgc gcgctccaag caagatgtac ggaggcgcac gcaaacgttc tacccaacat   15480
cccgtgcgtg ttcgcggaca ttttcgcgct ccatggggtg ccctcaaggg ccgcactcgc   15540
gttcgaacca ccgtcgatga tgtaatcgat caggtggttg ccgacgcccg taattatact   15600
cctactgcgc ctacatctac tgtggatgca gttattgaca gtgtagtggc tgacgctcgc   15660
aactatgctc gacgtaagag ccggcgaagg cgcattgcca gacgccaccg agctaccact   15720
gccatgcgag ccgcaagagc tctgctacga agagctagac gcgtggggcg aagagccatg   15780
cttagggcgg ccagacgtgc agcttcgggc gccagcgccg gcaggtcccg caggcaagca   15840
gccgctgtcg cagcggcgac tattgccgac atggcccaat cgcgaagagg caatgtatac   15900
tgggtgcgtg acgctgccac cggtcaacgt gtacccgtgc gcacccgtcc ccctcgcact   15960
tagaagatac tgagcagtct ccgatgttgt gtcccagcgg cgaggatgtc caagcgcaaa   16020
tacaaggaag aaatgctgca ggttatcgca cctgaagtct acggccaacc gttgaaggat   16080
gaaaaaaaac cccgcaaaat caagcgggtt aaaaaggaca aaaagaaga ggaagatggc   16140 gatgatgggc tggcggagtt tgtgcgcgag tttgccccac ggcgacgcgt gcaatggcgt   16200
gggcgcaaag ttcgacatgt gttgagacct ggaacttcgg tggtctttac acccggcgag   16260
cgttcaagcg ctacttttaa gcgttcctat gatgaggtgt acgggatga tgatattctt   16320 gagcaggcgg ctgaccgatt aggcgagttt gcttatggca agcgtagtag aataacttcc   16380
aaggatgaga cagtgtcaat acccttggat catggaaatc ccaccccctag tcttaaaccg   16440 gtcactttgc agcaagtgtt acccgtaact ccgcgaacag gtgttaaacg cgaaggtgaa   16500
```

```
gatttgtatc ccactatgca actgatggta cccaaacgcc agaagttgga ggacgttttg   16560
gagaaagtaa aagtggatcc agatattcaa cctgaggtta aagtgagacc cattaagcag   16620
gtagcgcctg gtctgggggt acaaactgta gacattaaga ttcccactga agtatggaa    16680 gtgcaaactg aacccgcaaa gcctactgcc acctccactg aagtgcaaac ggatccatgg   16740
atgcccatgc ctattacaac tgacgccgcc ggtcccactc gaagatcccg acgaaagtac   16800
ggtccagcaa gtctgttgat gcccaattat gttgtacacc catctattat tcctactcct   16860
ggttaccgag gcactcgcta ctatcgcagc cgaaacagta cctcccgccg tcgccgcaag   16920
acacctgcaa atcgcagtcg tcgccgtaga cgcacaagca aaccgactcc cggcgccctg   16980
gtgcggcaag tgtaccgcaa tggtagtgcg gaaccttga cactgccgcg tgcgcgttac    17040
catccgagta tcatcactta atcaatgttg ccgctgcctc cttgcagata tggccctcac   17100
ttgtcgcctt cgcgttccca tcactggtta ccgaggaaga aactcgcgcc gtagaagagg   17160
gatgttggga cgcggaatgc gacgctacag gcgacggcgt gctatccgca agcaattgcg   17220
gggtggtttt ttaccagcct taattccaat tatcgctgct gcaattggcg cgataccagg   17280
catagcttcc gtggcggttc aggcctcgca acgacattga cattggaaaa aaaacgtata   17340
aataaaaaaa aatacaatgg actctgacac tcctggtcct gtgactatgt tttcttagag   17400
atggaagaca tcaattttc atccttggct ccgcgacacg gcacgaagcc gtacatgggc    17460
acctggagcg acatcggcac gagccaactg aacgggggcg ccttcaattg gagcagtatc   17520
tggagcgggc ttaaaaattt tggctcaacc ataaaaacat acgggaacaa gcttggaac    17580 agcagtacag gacaggcgct tagaaataaa cttaaagacc agaacttcca acaaaaagta   17640
gtcgatggga tagcttccgg catcaatgga gtggtagatt tggctaacca ggctgtgcag   17700
aaaaagataa acagtcgttt ggacccgccg ccagcaaccc caggtgaaat gcaagtggag   17760
gaagaaattc ctccgccaga aaacgaggc gacaagcgtc cgcgtcccga tttggaagag    17820
acgctggtga cgcgcgtaga tgaaccgcct tcttatgagg aagcaacgaa gcttggaatg   17880
cccaccacta gaccgatagc cccaatggcc accggggtga tgaaaccttc tcagttgcat   17940
cgacccgtca ccttggattt gccccctccc cctgctgcta ctgctgtacc cgcttctaag   18000
cctgtcgctg ccccgaaacc agtcgccgta gccaggtcac gtcccggggg cgctcctcgt   18060
ccaaatgcgc actggcaaaa tactctgaac agcatcgtgg gtctaggcgt gcaaagtgta   18120
aaacgccgtc gctgcttta attaaatatg gagtagcgct taacttgcct atctgtgtat    18180
atgtgtcatt acacgccgtc acagcagcag aggaaaaaag gaagaggtcg tgcgtcgacg   18240
ctgagttact ttcaagatgg ccacccatc gatgctgccc caatgggcat acatgcacat    18300
cgccggacag gatgcttcgg agtacctgag tccgggtctg gtgcagttcg cccgcgccac   18360
agacacctac ttcaatctgg gaaataagtt tagaaatccc accgtagcgc cgacccacga   18420
tgtgaccacc gaccgtagcc agcggctcat gttgcgcttc gtgcccgttg accgggagga   18480
caatacatac tcttacaaag tgcggtacac cctggccgtg ggcgacaaca gagtgctgga   18540
tatggccagc acgttctttg acattagggg cgtgttggac agaggtccca gtttcaaacc   18600
ctattctggt acggcttaca actctctggc tcctaaaggc gctccaaatg catctcaatg   18660
gattgcaaaa ggcgtaccaa ctgcagcagc cgcaggcaat ggtgaagaag aacatgaaac   18720
agaggagaaa actgctactt acacttttgc caatgctcct gtaaaagccg aggctcaaat   18780
tacaaaagag ggcttaccaa taggtttgga gatttcagct gaaaacgaat ctaaacccat   18840
ctatgcagat aaactttatc agccagaacc tcaagtggga gatgaaactt ggactgacct   18900
```

```
agacggaaaa accgaagagt atggaggcag ggctctaaag cctactacta acatgaaacc    18960
ctgttacggg tcctatgcga agcctactaa tttaaaaggt ggtcaggcaa aaccgaaaaa    19020
ctcggaaccg tcgagtgaaa aaattgaata tgatattgac atggaatttt ttgataactc    19080
atcgcaaaga acaaacttca gtcctaaaat tgtcatgtat gcagaaaatg taggtttgga    19140
aacgccagac actcatgtag tgtacaaacc tggaacagaa gacacaagtt ccgaagctaa    19200
tttgggacaa cagtctatgc ccaacagacc caactacatt ggcttcagag ataactttat    19260
tggactcatg tactataaca gtactggtaa catggggggtg ctggctggtc aagcgtctca    19320
gttaaatgca gtggttgact tgcaggacag aaacacagaa cttctttacc aactcttgct    19380
tgactctctg ggcgacagaa ccagatactt tagcatgtgg aatcaggctg tggacagtta    19440
tgatcctgat gtacgtgtta ttgaaaatca tggtgtggaa gatgaacttc ccaactattg    19500
ttttccactg gacggcatag gtgttccaac aaccagttac aaatcaatag ttccaaatgg    19560
agaagataat aataattgga agaacctga agtaaatgga acaagtgaga tcggacaggg    19620
taatttgttt gccatggaaa ttaaccttca agccaatcta tggcgaagtt tcctttattc    19680
caatgtggct ctgtatctcc cagactcgta caaatacacc ccgtccaatg tcactcttcc    19740
agaaaacaaa aacacctacg actacatgaa cgggcgggtg gtgccgccat ctctagtaga    19800
cacctatgtg aacattggtg ccaggtggtc tctggatgcc atggacaatg tcaacccatt    19860
caaccaccac cgtaacgctg gcttgcgtta ccgatctatg cttctgggta acggacgtta    19920
tgtgcctttc cacatacaag tgcctcaaaa attcttcgct gttaaaaacc tgctgcttct    19980
cccaggctcc tacacttatg agtggaactt taggaaggat gtgaacatgg ttctacagag    20040
ttccctcggt aacgacctgc gggtagatgg cgccagcatc agtttcacga gcatcaacct    20100
ctatgctact ttttccccca tggctcacaa caccgcttcc acccttgaag ccatgctgcg    20160
gaatgacacc aatgatcagt cattcaacga ctacctatct gcagctaaca tgctctaccc    20220
cattcctgcc aatgcaacca atattcccat ttccattcct tctcgcaact gggcggcttt    20280
cagaggctgg tcatttacca gactgaaaac caaagaaact ccctcttttgg ggtctggatt    20340 tgaccccctac tttgtctatt ctggttctat tccctacctg gatggtacct tctacctgaa    20400
ccacactttt aagaaggttt ccatcatgtt tgactcttca gtgagctggc ctggaaatga    20460
caggttacta tctcctaacg aatttgaaat aaagcgcact gtggatggcg aaggctacaa    20520
cgtagcccaa tgcaacatga ccaaagactg gttcttggta cagatgctcg ccaactacaa    20580
catcggctat cagggcttct acattccaga aggatacaaa gatcgcatgt attcatttft    20640 cagaaacttc cagcccatga gcaggcaggt ggttgatgag gtcaattaca aagacttcaa    20700
ggccgtcgcc ataccctacc aacacaacaa ctctggcttt gtgggttaca tggctccgac    20760
catgcgccaa ggtcaaccct atcccgctaa ctatccctat ccactcattg aacaactgc    20820 cgtaaatagt gttacgcaga aaagttctt gtgtgacaga accatgtggc gcataccgtt    20880
ctcgagcaac ttcatgtcta tgggggccct tacagacttg gacagaaata tgctctatgc    20940
caactcagct catgctctgg acatgacctt tgaggtggat cccatggatg agcccaccct    21000
gctttatctt ctcttcgaag ttttcgacgt ggtcagagtg catcagccac accgcggcat    21060
catcgaggca gtctacctgc gtacaccgtt ctcggccggt aacgctacca cgtaagaagc    21120
ttcttgcttc ttgcaaatag cagctgcaac catggcctgc ggatcccaaa acggctccag    21180
cgagcaagag ctcagagcca ttgtccaaga cctgggttgc ggaccctatt ttttgggaac    21240
ctacgataag cgcttcccgg ggttcatggc ccccgataag ctcgcctgtg ccattgtaaa    21300
```

```
tacggccgga cgtgagacgg ggggagagca ctggttggct ttcggttgga acccacgttc   21360
taacacctgc tacctttttg atccttttgg attctcggat gatcgtctca aacagattta   21420
ccagtttgaa tatgagggtc tcctgcgccg cagcgctctt gctaccaagg accgctgtat   21480
tacgctggaa aaatctaccc agaccgtgca gggcccccgt tctgccgcct gcggactttt   21540
ctgctgcatg ttccttcacg cctttgtgca ctggcctgac cgtcccatgg acggaaaccc   21600
caccatgaaa ttgctaactg gagtgccaaa caacatgctt cattctccta aagtccagcc   21660
caccctgtgt gacaatcaaa aagcactcta ccattttctt aatacccatt cgccttattt   21720
tcgctctcat cgtacacaca tcgaaagggc cactgcgttc gaccgtatgg atgttcaata   21780
atgactcatg taaacaacgt gttcaataaa catcacttta ttttttttaca tgtatcaagg   21840 ctctggatta cttatttatt tacaagtcga atgggttctg acgagaatca gaatgacccg   21900
caggcagtga tacgttgcgg aactgatact tgggttgcca cttgaattcg ggaatcacca   21960
acttgggaac cggtatatcg ggcaggatgt cactccacag ctttctggtc agctgcaaag   22020
ctccaagcag gtcaggagcc gaaatcttga aatcacaatt aggaccagtg ctctgagcgc   22080
gagagttgcg gtacaccgga ttgcagcact gaaacaccat cagcgacgga tgtctcacgc   22140
ttgccagcac ggtgggatct gcaatcatgc ccacatccaa atcttcagca ttggcaatgc   22200
tgaacggggt catcttgcag gtctgcctac ccatggcggg cacccaatta ggcttgtggt   22260
tgcaatcgca gtgcagggggg atcagtatca tcttggcctg atcctgtctg attcctggat   22320
acacggctct catgaaagca tcatattgct tgaaagcctg ctgggctttta ctaccctcgg   22380 tataaaacat cccgcaggac ctgctcgaaa actggttagc tgcacagccg gcatcattca   22440
cacagcagcg ggcgtcattg ttggctattt gcaccacact tctgccccag cggttttggg   22500 tgatttggt tcgctcggga ttctcccttta aggctcgttg tccgttctcg ctggccacat   22560
ccatctcgat aatctgctcc ttctgaatca taatattgcc atgcaggcac ttcagcttgc   22620
cctcataatc attgcagcca tgaggccaca acgcacagcc tgtacattcc caattatggt   22680
gggcgatctg agaaaaagaa tgtatcattc cctgcagaaa tcttcccatc atcgtgctca   22740
gtgtcttgtg actagtgaaa gttaactgga tgcctcggtg ctcttcgttt acgtactggt   22800
gacagatgcg cttgtattgt tcgtgttgct caggcattag tttaaaacag gttctaagtt   22860
cgttatccag cctgtacttc tccatcagca gacacatcac ttccatgcct ttctcccaag   22920
cagacaccag gggcaagcta atcggattct taacagtgca ggcagcagct cctttagcca   22980
gagggtcatc tttagcgatc ttctcaatgc ttctttttgcc atccttctca acgatgcgca   23040
cgggcgggta gctgaaaccc actgctacaa gttgcgcctc ttctctttct tcttcgctgt   23100
cttgactgat gtcttgcatg gggatatgtt tggtcttcct tggcttcttt ttgggggggta   23160 tcggaggagg aggactgtcg ctccgttccg gagacaggga ggattgtgac gtttcgctca   23220
ccattaccaa ctgactgtcg gtagaagaac ctgaccccac acggcgacag gtgtttttct   23280
tcgggggcag aggtggaggc gattgcgaag ggctgcggtc cgacctggaa ggcggatgac   23340
tggcagaacc ccttccgcgt tcggggggtgt gctccctgtg gcggtcgctt aactgatttc   23400
cttcgcggct ggccattgtg ttctcctagg cagagaaaca acagacatgg aaactcagcc   23460
attgctgtca acatcgccac gagtgccatc acatctcgtc ctcagcgacg aggaaaagga   23520
gcagagctta agcattccac cgcccagtcc tgccaccacc tctaccctag aagataagga   23580
ggtcgacgca tctcatgaca tgcagaataa aaaagcgaaa gagtctgaga cagacatcga   23640
gcaagacccg ggctatgtga caccggtgga acacgaggaa gagttgaaac gctttctaga   23700
```

```
gagagaggat gaaaactgcc caaaacagcg agcagataac tatcaccaag atgctggaaa   23760
tagggatcag aacaccgact acctcatagg gcttgacggg gaagacgcgc tccttaaaca   23820
tctagcaaga cagtcgctca tagtcaagga tgcattattg gacagaactg aagtgcccat   23880
cagtgtggaa gagctcagct gcgcctacga gcttaacctt ttttcacctc gtactccccc   23940
caaacgtcag ccaaacggca cctgcgagcc aaatcctcgc ttaaactttt atccagcttt   24000
tgctgtgcca gaagtactgg ctacctatca catcttttt aaaaatcaaa aaattccagt   24060
ctcctgccgc gctaatcgca cccgcgccga tgccctactc aatctgggac ctggttcacg   24120
cttacctgat atagcttcct tggaagaggt tccaaagatc ttcgagggtc tgggcaataa   24180
tgagactcgg gccgcaaatg ctctgcaaaa gggagaaaat ggcatggatg agcatcacag   24240
cgttctggtg gaattggaag gcgataatgc cagactcgca gtactcaagc gaagcgtcga   24300
ggtcacacac ttcgcatatc ccgctgtcaa cctgccccct aaagtcatga cggcggtcat   24360
ggaccagtta ctcattaagc gcgcaagtcc cctttcagaa gacatgcatg acccagatgc   24420
ctgtgatgag ggtaaaccag tggtcagtga tgagcagcta acccgatggc tgggcaccga   24480
ctctccccgg gatttggaag agcgtcgcaa gcttatgatg gccgtggtgc tggttaccgt   24540
agaactagag tgtctccgac gtttctttac cgattcagaa accttgcgca aactcgaaga   24600
gaatctgcac tacacttta gacacggctt tgtgcggcag gcatgcaaga tatctaacgt   24660
ggaactcacc aacctggttt cctacatggg tattctgcat gagaatcgcc taggacaaag   24720
cgtgctgcac agcaccctta gggggaagc ccgccgtgat tacatccgcg attgtgtcta   24780
tctctacctg tgccacacgt ggcaaaccgg catgggtgta tggcagcaat gtttagaaga   24840
acagaacttg aaagagcttg acaagctctt acagaaatct cttaaggttc tgtggacagg   24900
gttcgacgag cgcaccgtcg cttccgacct ggcagacctc atcttcccag agcgtctcag   24960
ggttactttg cgaaacggat tgcctgactt tatgagccag agcatgctta acaattttcg   25020
ctctttcatc ctggaacgct ccggtatcct gcccgccacc tgctgcgcac tgccctccga   25080
ctttgtgcct ctcacctacc gcgagtgccc ccgccgcta tggagtcact gctacctgtt   25140
ccgtctggcc aactatctct cctaccactc ggatgtgatc gaggatgtga gcggagacgg   25200
cttgctggag tgccactgcc gctgcaatct gtgcacgccc caccggtccc tagcttgcaa   25260
cccccagttg atgagcgaaa cccagataat aggcacctt gaattgcaag gccccagcag   25320
ccaaggcgat gggtcttctc ctgggcaaag tttaaaactg accccgggac tgtggacctc   25380
cgcctacttg cgcaagtttg ctccggaaga ttaccacccc tatgaaatca gttctatga   25440 ggaccaatca cagcctccaa aggccgaact ttcggcttgc gtcatcaccc aggggcaat   25500 tctggcccaa ttgcaagcca tccaaaaatc ccgccaagaa tttctactga aaagggtaa   25560 gggggtctac cttgacccc agaccggcga ggaactcaac acaaggttcc ctcaggatgt   25620
cccaacgacg agaaaacaag aagttgaagg tgcagccgcc gcccccagaa gatatggagg   25680
aagattggga cagtcaggca gaggaggcgg aggaggacag tctggaggac agtctggagg   25740
aagacagttt ggaggaggaa acgaggagg cagaggaggt ggaagaagta accgccgaca   25800
aacagttatc ctcggctgcg gagacaagca acagcgctac catctccgct ccgagtcgag   25860
gaacccggcg gcgtcccagc agtagatggg acgagaccgg acgcttcccg aacccaacca   25920
gcgcttccaa gaccggtaag aaggatcggc agggatacaa gtcctggcgg ggcataaga   25980 atgccatcat ctcctgcttg catgagtgcg ggggcaacat atccttcacg cggcgctact   26040
tgctattcca ccatggggtg aactttccgc gcaatgtttt gcattactac cgtcacctcc   26100
```

```
acagcccta ctatagccag caaatcccga cagtctcgac agataaagac agcggcggcg    26160
acctccaaca gaaaaccagc agcggcagtt agaaaataca caacaagtgc agcaacagga    26220
ggattaaaga ttacagccaa cgagccagcg caaacccgag agttaagaaa tcggatcttt    26280
ccaaccctgt atgccatctt ccagcagagt cggggtcaag agcaggaact gaaaataaaa    26340
aaccgatctc tgcgttcgct caccagaagt tgtttgtatc acaagagcga agatcaactt    26400
cagcgcactc tcgaggacgc cgaggctctc ttcaacaagt actgcgcgct gactcttaaa    26460
gagtaggcag cgaccgcgct tattcaaaaa aggcgggaat tacatcatcc tcgacatgag    26520
taaagaaatt cccacgcctt acatgtggag ttatcaaccc caaatgggat tggcagcagg    26580
cgcctcccag gactactcca cccgcatgaa ttggctcagc gccgggcctt ctatgatttc    26640
tcgagttaat gatatacgcg cctaccgaaa ccaaatactt ttggaacagt cagctcttac    26700
caccacgccc cgccaacacc ttaatcccag aaattggccc gccgcctag tgtaccagga    26760
aagtcccgct cccaccactg tattacttcc tcgagacgcc caggccgaag tccaaatgac    26820
taatgcaggt gcgcagttag ctggcggctc caccctatgt cgtcacaggc ctcggcataa    26880
tataaaacgc ctgatgatca gaggccgagg tatccagctc aacgacgagt cggtgagctc    26940
tccgcttggt ctacgaccag acggaatctt tcagattgcc ggctgcggga gatcttcctt    27000
caccccctcgt caggctgttc tgactttgga agttcgtct tcgcaacccc gctcgggcgg    27060
aatcgggacc gttcaatttg tagaggagtt tactccctct gtctacttca accccttctc    27120
cggatctcct gggcactacc cggacgagtt cataccgaac ttcgacgcga ttagcgagtc    27180
agtggacggt tacgattgat gtctggtgac gcggctgagc tatctcggct gcgacatcta    27240
gaccactgcc gccgctttcg ctgctttgcc cgggaactta ttgagttcat ctacttcgaa    27300
ctccccaagg atcaccctca aggtccggcc cacgagtgc ggattactat cgaaggcaaa    27360
atagactctc gcctgcaacg aattttctcc cagcggcccg tgctgatcga gcgagaccag    27420
ggaaacacca cggtttccat ctactgcatt tgtaatcacc ccggattgca tgaaagcctt    27480
tgctgtctta tgtgtactga gtttaataaa aactgaatta agactctcct acggactgcc    27540
gcttcttcaa cccggatttt acaaccagaa gaacaaaact tttcctgtcg tccaggactc    27600
tgttaacttc accttttccta ctcacaaact agaagctcaa cgactacacc gcttttccag    27660
aagcattttc cctactaata ctactttcaa aaccggaggt gagctccacg gtctccctac    27720
agaaacccct tgggtggaag cgggccttgt agtactagga attcttgcgg gtgggcttgt    27780
gattattctt tgctacctat acacaccttg cttcactttc ctagtggtgt tgtggtattg    27840
gtttaaaaaa tggggcccat actagtcttg cttgttttac tttcgctttt ggaaccgggt    27900
tctgccaatt acgatccatg tctagacttt gacccagaaa actgcacact acttttgca    27960
cccgacacaa gccgcatctg tggagttctt attaagtgcg gatgggaatg caggtccgtt    28020
gaaattacac acaataacaa aacctggaac aataccttat ccaccacatg ggagccagga    28080
gttcccgagt ggtacactgt ctctgtccga ggtcctgacg gttccatccg cattagtaac    28140
aacactttca ttttttctga aatgtgcgat ctggccatgt tcatgagcaa acagtattct    28200
ctatggcctc ctagcaagga caacatcgta acgttctcca ttgcttattg cttgtgcgct    28260
tgccttctta ctgctttact gtgcgtatgc atacacctgc ttgtaaccac tcgcatcaaa    28320
aacgccaata acaaagaaaa aatgccttaa cctcttttctg tttacagaca tggcttctct    28380
tacatctctc atatttgtca gcattgtcac tgccgctcac ggacaaacag tcgtctctat    28440
cccactagga cataattaca ctctcataggg acccccaatc acttcagagg tcatctggac    28500
```

```
caaactggga agcgttgatt actttgatat aatctgtaac aaaacaaaac caataatagt    28560
aacttgcaac atacaaaatc ttacattgat taatgttagc aaagtttaca gcggttacta    28620
ttatggttat gacagataca gtagtcaata tagaaattac ttggttcgtg ttacccagtt    28680
gaaaaccacg aaaatgccaa atatggcaaa gattcgatcc gatgacaatt ctctagaaac    28740
ttttacatct cccaccacac ccgacgaaaa aaacatccca gattcaatga ttgcaattgt    28800
tgcagcggtg gcagtggtga tggcactaat aataatatgc atgcttttat atgcttgtcg    28860
ctacaaaaag tttcatccta aaaaacaaga tctcctacta aggcttaaca tttaatttct    28920
ttttatacag ccatggtttc cactaccaca ttccttatgc ttactagtct cgcaactctg    28980
acttctgctc gctcacacct cactgtaact ataggctcaa actgcacact aaaaggacct    29040
caaggtggtc atgtcttttg gtggagaata tatgacaatg gatggtttac aaaaccatgt    29100
gaccaacctg gtagattttt ctgcaacggc agagacctaa ccattatcaa cgtgacagca    29160
aatgacaaag gcttctatta tggaaccgac tataaaagta gtttagatta taacattatt    29220
gtactgccat ctaccactcc agcaccccgc acaactactt tctctagcag cagtgtcgct    29280
aacaatacaa tttccaatcc aaccttttgcc gcgcttttaa aacgcactgt gaataattct    29340
acaacttcac atacaacaat ttccacttca acaatcagca tcatcgctgc agtgacaatt    29400
ggaatatcta ttcttgtttt taccataacc tactacgcct gctgctatag aaaagacaaa    29460
cataaaggtg atccattact tagatttgat atttaatttg ttcttttttt ttatttacag    29520
tatggtgaac accaatcatg gtacctagaa atttcttctt caccatactc atctgtgctt    29580
ttaatgtttg cgctactttc acagcagtag ccacagcaac cccagactgt ataggagcat    29640
ttgcttccta tgcactttt gcttttgtta cttgcatctg cgtatgtagc atagtctgcc    29700
tggttattaa tttttttccaa cttctagact ggatccttgt gcgaattgcc tacctgcgcc    29760
accatcccga ataccgcaac caaaatatcg cggcacttct tagactcatc taaaaccatg    29820
caggctatac taccaatatt tttgcttcta ttgcttccct acgctgtctc aaccccagct    29880
gcctatagta ctccaccaga acaccttaga aaatgcaaat tccaacaacc gtggtcattt    29940
cttgcttgct atcgagaaaa atcagaaatc cccccaaatt taataatgat tgctggaata    30000
attaatataa tctgttgcac cataatttca tttttgatat accccctatt tgattttggc    30060
tggaatgctc ccaatgcaca tgatcatcca caagacccag aggaacacat tcccccacaa    30120
aacatgcaac atccaatagc gctaatagat tacgaaagtg aaccacaacc cccactactc    30180
cctgctatta gttacttcaa cctaaccggc ggagatgact gaaacactca ccacctccaa    30240
ttccgccgag gatctgctcg atatggacgg ccgcgtctca gaacaacgac ttgcccaact    30300
acgcatccgc cagcagcagg aacgcgtggc caaagagctc agagatgtca tccaaattca    30360
ccaatgcaaa aaaggcatat tctgtttggt aaaacaagcc aagatatcct acgagatcac    30420
cgctactgac catcgcctct cttacgaact tggcccccaa cgacaaaaat ttacctgcat    30480
ggtgggaatc aaccccatag ttatcaccca acaaagtgga gatactaagg gttgcattca    30540
ctgctcctgc gattccatcg agtgcaccta caccctgctg aagacctat gcggcctaag    30600 agacctgcta ccaatgaatt aaaaaaaaat gattaataaa aaatcactta cttgaaatca    30660
gcaataaggt ctctgttgaa attttctccc agcagcacct cacttccctc ttcccaactc    30720
tggtattcta aaccccgttc agcggcatac tttctccata cttttaaggg gatgtcaaat    30780
tttagctcct ctcctgtacc cacaatcttc atgtctttct tcccagatga ccaagagagt    30840
ccggctcagt gactccttca accctgtcta cccctatgaa gatgaaagca cctcccaaca    30900
```

```
cccctttata aacccagggt ttatttcccc aaatggcttc acacaaagcc cagacggagt    30960
tcttacttta aaatgtttaa ccccactaac aaccacaggc ggatctctac agctaaaagt    31020
gggaggggga cttacagtgg atgacactga tggtacctta caagaaaaca tacgtgctac    31080
agcacccatt actaaaaata atcactctgt agaactatcc attggaaatg gattagaaac    31140
tcaaaacaat aaactatgtg ccaaattggg aaatgggtta aaatttaaca acggtgacat    31200
ttgtataaag gatagtatta acaccttatg gactggaata aaccctccac ctaactgtca    31260
aattgtggaa aacactaata caaatgatgg caaacttact ttagtattag taaaaaatgg    31320
agggcttgtt aatggctacg tgtctctagt tggtgtatca gacactgtga accaaatgtt    31380
cacacaaaag acagcaaaca tccaattaag attatatttt gactcttctg gaaatctatt    31440
aactgaggaa tcagacttaa aaattccact taaaaataaa tcttctacag cgaccagtga    31500
aactgtagcc agcagcaaag cctttatgcc aagtactaca gcttatccct tcaacaccac    31560
tactagggat agtgaaaact acattcatgg aatatgttac tacatgacta gttatgatag    31620
aagtctattt cccttgaaca tttctataat gctaaacagc cgtatgattt cttccaatgt    31680
tgcctatgcc atacaatttg aatggaatct aaatgcaagt gaatctccag aaagcaacat    31740
agctacgctg accacatccc cctttttctt ttcttacatt acagaagacg acaactaaaa    31800
taaagtttaa gtgttttat ttaaaatcac aaaattcgag tagttatttt gcctccacct    31860
tcccatttga cagaatacac caatctctcc ccacgcacag ctttaaacat ttggatacca    31920
ttagagatag acattgtttt agattccaca ttccaaacag tttcagagcg agccaatctg    31980
gggtcagtga tagataaaaa tccatcgcga tagtctttta aagcgctttc acagtccaac    32040
tgctgcggat gcgactccgg agtttggatc acggtcatct ggaagaagaa cgatgggaat    32100
cataatccga aaacggtatc ggacgattgt gtctcatcaa acccacaagc agccgctgtc    32160
tgcgtcgctc cgtgcgactg ctgtttatgg gatcagggtc cacagtttcc tgaagcatga    32220
ttttaatagc ccttaacatc aacttttctgg tgcgatgcgc gcagcaacgc attctgattt    32280
cactcaaatc tttgcagtag gtacaacaca ttattacaat attgtttaat aaaccataat    32340
taaaagcgct ccagccaaaa ctcatatctg atataatcgc ccctgcatga ccatcatacc    32400
aaagtttaat ataaattaaa tgacgttccc tcaaaaacac actacccaca tacatgatct    32460
cttttggcat gtgcatatta acaatctgtc tgtaccatgg acaacgttgg ttaatcatgc    32520
aacccaatat aaccttccgg aaccacactg ccaacaccgc tcccccagcc atgcattgaa    32580
gtgaaccctg ctgattacaa tgacaatgaa gaacccaatt ctctcgaccg tgaatcactt    32640
gagaatgaaa atatctata gtggcacaac atagacataa atgcatgcat cttctcataa    32700
tttttaactc ctcaggattt agaaacatat cccaggaat aggaagctct tgcagaacag    32760
taaagctggc agaacaagga agaccacgaa cacaacttac actatgcata gtcatagtat    32820
cacaatctgg caacagcggg tggtcttcag tcatagaagc tcgggtttca ttttcctcac    32880
aacgtggtaa ctgggctctg gtgtaagggt gatgtctggc gcatgatgtc gagcgtgcgc    32940
gcaaccttgt cataatggag ttgcttcctg acattctcgt attttgtata gcaaaacgcg    33000
gccctggcag aacacactct tcttcgcctt ctatcctgcc gcttagcgtg ttccgtgtga    33060
tagttcaagt acagccacac tcttaagttg gtcaaaagaa tgctggcttc agttgtaatc    33120
aaaactccat cgcatctaat tgttctgagg aaatcatcca cggtagcata tgcaaatccc    33180
aaccaagcaa tgcaactgga ttgcgtttca agcaggagag gagagggaag agacggaaga    33240
accatgttaa ttttttattcc aaacgatctc gcagtacttc aaattgtaga tcgcgcagat    33300
```

-continued

```
ggcatctctc gccccactg tgttggtgaa aaagcacagc taaatcaaaa gaaatgcgat    33360
tttcaaggtg ctcaacggtg gcttccaaca aagcctccac gcgcacatcc aagaacaaaa    33420
gaataccaaa agaaggagca ttttctaact cctcaatcat catattacat tcctgcacca    33480
ttcccagata attttcagct ttccagcctt gaattattcg tgtcagttct tgtggtaaat    33540
ccaatccaca cattacaaac aggtcccgga gggcgccctc caccaccatt cttaaacaca    33600
ccctcataat gacaaaatat cttgctcctg tgtcacctgt agcgaattga gaatggcaac    33660
atcaattgac atgccttgg ctctaagttc ttctttaagt tctagttgta aaaactctct    33720
catattatca ccaaactgct tagccagaag cccccggga acaagagcag gggacgctac    33780
agtgcagtac aagcgcagac ctccccaatt ggctccagca aaaacaagat tggaataagc    33840
atattgggaa ccaccagtaa tatcatcgaa gttgctggaa atataatcag gcagagtttc    33900
ttgtagaaat tgaataaaag aaaaatttgc caaaaaaaca ttcaaaacct ctgggatgca    33960
aatgcaatag gttaccgcgc tgcgctccaa cattgttagt tttgaattag tctgcaaaaa    34020
taaaaaaaaa acaagcgtca tatcatagta gcctgacgaa caggtggata aatcagtctt    34080
tccatcacaa gacaagccac agggtctcca gctcgaccct cgtaaaacct gtcatcgtga    34140
ttaaacaaca gcaccgaaag ttcctcgcgg tgaccagcat gaataagtct tgatgaagca    34200
tacaatccag acatgttagc atcagttaag gagaaaaaac agccaacata gcctttgggt    34260
ataattatgc ttaatcgtaa gtatagcaaa gccacccctc gcggatacaa agtaaaaggc    34320
acaggagaat aaaaaatata attatttctc tgctgctgtt taggcaacgt cgccccggt    34380 ccctctaaat acacatacaa agcctcatca gccatggctt accagagaaa gtacagcggg    34440
cacacaaacc acaagctcta aagtcactct ccaacctstc cacaatatat atacacaagc    34500
cctaaactga cgtaatggga ctaaagtgta aaaaatcccg ccaaacccaa cacacacccc    34560
gaaactgcgt caccagggaa aagtacagtt tcacttccgc aatcccaaca agcgtcactt    34620
cctctttctc acggtacgtc acatcccatt aacttacaac gtcattttcc cacggccgcg    34680 ccgcccttt taaccgttaa ccccacagcc aatcaccaca cggcccacac ttttaaaat    34740 cacctcattt acatattggc accattccat ctataaggta tattattgat gatg           34794
```

ADENOVIRUS VECTOR

TECHNICAL FIELD

The present invention relates to an adenovirus vector that is utilized when, for example, transfecting a gene of interest into a target cell.

BACKGROUND ART

In 1953, adenoviruses were separated from a culture solution of pediatric tonsil or adenoid cells. The existence of 80 or more adenovirus serotypes that are infected with humans, birds, cattle, monkeys, dogs, mice, or pigs as a host has been discovered to date. Up to the present, 51 or more types of adenovirus serotypes that are infected with humans as a host have been discovered, and adenovirus type 2 and type 5 are used as vectors for gene therapy.

Adenovirus type 5 is a non-enveloped and regular icosahedron with 252 capsomeres. Among them, the 12 capsomeres located at the peak of the icosahedron are referred to as "pentons" (composed of Penton bases and fibers) having projected structures and the other 240 capsomeres are referred to as "hexons." Viruses infiltrate (infect) cells as follows. Fibers bind to the CAR receptors (for details, please refer to Bergelson J M et al., Isolation of a common receptor for Coxsackie B viruses and adenoviruses 2 and 5, Science 275: 1320-1323, 1997) and the RGD motifs of the penton bases then bind to the integrins on the cell surfaces (Bai M, Harfe B, Freimuth P, Mutations that alter an Arg-Gly-Asp (RGD) sequence in the adenovirus type 2 penton base protein abolish its cell-rounding activity and delay virus reproduction in flat cells, J. Virol. 67: 5198-5205, 1993; Wickham T J et al., Integrins $\alpha v\beta 3$ and $\alpha v\beta 5$ promote adenovirus internalization but not virus attachment, Cell 73: 309-319, 1993). Viruses that reach the endosomes alter capsid protein structures under acidic conditions, disrupt the endosomes, and infiltrate the cytoplasm. Accordingly, the first step of infection is the binding of viral fibers to the CAR receptors on the cell surfaces, and the infection range for a vector is considered to be capable of being varied via modification of fibers (Paillard, F., Dressing up adenoviruses to modify their tropism, Hum. Gene Ther. 10:2575-2576, 1999).

Adenovirus type 35 was first discovered in urine of patients such as those who had undergone kidney transplantation, those who had undergone marrow graft, and those with AIDS. Infection therewith is said to cause acute hemorrhagic cystitis and to infect the kidney. At present, a receptor for adenovirus type 35 infection is not yet known.

DISCLOSURE OF THE INVENTION

Examples of known vectors that are used when transfecting a foreign gene into a target cell are adenovirus types 2, 5, and 7 that are infected with humans as a host and chimpanzees-adenoviruse, mouse-adenoviruse, dog-adenoviruse, sheep-adenoviruse and bird-adenoviruse that are infected with non-humans as a host.

However, vectors utilizing adenoviruses as mentioned above have insufficient infectivity depending on the target cell type or insufficient gene transfection efficiency. Thus, such vectors have not been able to accomplish the end desired.

Accordingly, an object of the present invention is to provide an adenovirus vector that has excellent gene transfection efficiency on specific cell lines, particularly on hematopoietic cells, ES cells, pluripotent stem cells, blood stem cells, and tissue stem cells.

The present invention that has attained the above object includes the following.

1. An adenovirus type 35 vector, which is derived from the adenovirus type 35 genome at least by partial or total deletion of the E1 region therefrom.

2. The adenovirus type 35 vector according to 1. above, wherein the E1 protein encoded by the aforementioned E1 region is rendered incapable of being expressed or is functionally defective.

3. The adenovirus type 35 vector according to 1. or 2. above, wherein part of the E1 region is equivalent to the region between nucleotides 367 and 2,917 of the adenovirus type 35 genome.

4. The adenovirus type 35 vector according to 1. or 2. above, wherein part of the E1 region is equivalent to the region between nucleotides 367 and 3,375 of the adenovirus type 35 genome.

5. The adenovirus type 35 vector according to 1. above, wherein the E3 region is further partially or totally deleted from the adenovirus type 35 genome.

6. The adenovirus type 35 vector according to 5. above, wherein part of the E3 region is equivalent to the region between nucleotides 2,776 and 29,732 of the adenovirus type 35 genome.

7. The adenovirus type 35 vector according to any one of 1. to 6. above, wherein a foreign gene is inserted into a site that lacks part or all of the E1 and/or E3 regions.

8. A method for producing an adenovirus type 35 vector comprising the following steps of:

(1) preparing an adenovirus type 35 vector derived from the adenovirus type 35 genome by partially or totally deleting the E1 region therefrom;

(2) allowing the prepared vector to infect and proliferate in adenovirus E1 protein- and E4 protein-expressing cells; and (3) recovering the proliferated vectors.

9. The method for producing an adenovirus type 35 vector according to 8. above, wherein step (1) further comprises a step of partially or totally deleting the E 3 region.

10. The method for producing an adenovirus type 35 vector according to 8. above, which further comprises a step of inserting a foreign gene into a deleted site between step (1) and step (2).

11. The method for producing an adenovirus type 35 vector according to 8. above, wherein the cell employed in step (2) is of the 293-cell line.

12. An adenovirus type 35 vector, which is obtained by the method for producing an adenovirus type 35 vector according to any one of 8. to 11. above.

13. A method for producing an adenovirus type 35 vector comprising the following steps of:

(1) preparing part of the adenovirus type 35 genome that lacks part or all of the E1 region;

(2) ligating the part of the adenovirus type 35 genome to the remaining portion of the adenovirus type 35 genome and thereby preparing an adenovirus type 35 vector derived from the adenovirus type 35 genome by partial or total deletion of the E1 region therefrom;

(3) allowing the prepared vector to infect and proliferate in adenovirus E1 protein- and E4 protein-expressing cells; and (4) recovering the proliferated vectors.

14. The method for producing an adenovirus type 35 vector according to 13. above, wherein step (1) or (2) further comprises a step of partially or totally deleting the E 3 region.

15. The method for producing an adenovirus type 35 vector according to 13. above, wherein step (1) further comprises a step of inserting a foreign gene into a deleted site.

16. The method for producing an adenovirus type 35 vector according to 13. above, wherein the cell employed in step (3) is of the 293-cell line.

17. The method for producing an adenovirus type 35 vector according to 13. above, wherein the part of the adenovirus type 35 genome mentioned in (1) is equivalent to a region lacking the region between nucleotides 367 to 2,917 or that between nucleotides 367 to 3,375 of the region between nucleotides 1 to 7,932.

18. An adenovirus type 35 vector, which is obtained by the method for producing an adenovirus type 35 vector according to any one of 13. to 17. above.

19. A method for gene transfection, wherein the adenovirus type 35 vector according to any one of 1. to 7., 12., and 18. above is allowed to infect a target cell.

20. The method for gene transfection according to 19. above, wherein the target cell is selected from the group consisting of hematopoietic cells, blood stem cells, ES cells, pluripotent stem cells, and tissue stem cells.

21. The method for gene transfection according to 19. above, wherein the target cell is a CD34$^+$ cell.

Hereafter, the present invention is described in detail.

The adenovirus vector according to the present invention is derived from the adenovirus type 35 genome at least by partial or total deletion of the E1 region therefrom. In the following description, a site or region lacking part or all of the E1 region may be referred to as the "E1-deleted region." In the present invention, the term "lacking part or all of the E1 region" refers to, but is not limited to, a situation where the E1 protein encoded by the E1 region is rendered incapable of being expressed or is functionally defective. Also, the adenovirus vector according to the present invention may consist of part of the adenovirus type 35 genome as long as the E1-deleted region is present. Alternatively, the adenovirus vector according to the present invention may consist of the entire adenovirus type 35 genome having the E1-deleted region. In the description and drawings below, adenovirus type 35 may be abbreviated as "Ad35."

An adenovirus vector having the E1-deleted region and consisting of part of the adenovirus type 35 genome can be obtained by, for example, cleaving a fragment comprising the E1 region of the adenovirus type 35 genome with a restriction enzyme, deleting the E1 region from the cleavage fragment to obtain part of the adenovirus type 35 genome, ligating the resultant to a given vector, and transfecting the ligation product into E1 protein- and E4 protein- expressing 293-cell lines, followed by recovery from the cells.

A specific example of the adenovirus vector consisting of part of the adenovirus type 35 genome is one consisting of a nucleotide sequence lacking the region between nucleotides 367 to 2,917 (E1-deleted region) of the region between nucleotides 1 to 7,932 of the adenovirus type 35 genome. Numbers in the nucleotide sequence of the adenovirus type 35 genome are based on the nucleotide sequence that is registered in the Gene Bank database under the accession number AX049983. The nucleotide sequence of the adenovirus type 35 genome is shown in SEQ ID NO: 1.

The E1 region of the adenovirus type 35 genome refers to a region that encodes the E1 protein, which is essential for proliferation of common adenoviruses. Part of the E1 region of the adenovirus type 35 genome is equivalent to the region between nucleotides 367 and 2,917 in the nucleotide sequence of the adenovirus type 35 genome and is present in a 2,550 bp fragment that is generated upon treatment of the adenovirus type 35 genome with restriction enzymes AccI and PacI. Alternatively, part of the E1 region is equivalent to the region between nucleotides 367 and 3,375 in the nucleotide sequence of the adenovirus type 35 genome and is present in a 3,008 bp fragment that is generated upon treatment of the adenovirus type 35 genome with restriction enzymes AccI and BamHI. Further, the E1 region is constituted by the E1a and E1b regions.

In particular, the term "E1-deleted region" refers to an E1 protein-encoding region that is functionally defective. The term "functionally defective" refers to the fact that, for example, the E1 protein is not allowed to express in a manner such that it functions in a host cell. Accordingly, the adenovirus vector according to the present invention does not necessarily lack the entire E1 region. Instead, it may have part of the E1 region. Specifically, the adenovirus vector according to the present invention may comprise part of the E1 region of the adenovirus type 35 genome as long as the E1 protein that functions in a host cell is not expressed. The "E1-deleted region" may lack all or part of the E1a or E1b region, may lack all of both regions, or may lack a portion that spans both regions, as long as an E1 protein-encoding region is functionally defective.

The adenovirus vector according to the present invention may be constituted by part or all of the adenovirus type 35 genome that lacks the E3 region as well as the E1 region. The E3 region in the adenovirus type 35 genome can be deleted by treatment the adenovirus type 35 genome with EcoRI and BamHI, and removing a site equivalent to the region between nucleotides 27,760 and 29,732. Use of the adenovirus type 35 genome that lacks the E3 region as well as the E1 region enables insertion of a large-size foreign nucleotide sequence into the E1-deleted region.

Further, the adenovirus vector according to the present invention has the E1-deleted region and may have attenuated immune responses due to partial deletion of genes that are present in the adenovirus type 35 genome. In other words, the adenovirus vector according to the present invention may be a so-called "gutted" ("gutless") adenovirus vector having the E1-deleted region and consisting of part of the adenovirus type 35 genome.

The recombinant adenovirus vector according to the present invention has a foreign nucleotide sequence in the E1-deleted region and comprises the entire adenovirus type 35 genomes excluding the E1-deleted region. This recombinant adenovirus vector can be prepared using the adenovirus vector according to the present invention. Specifically, such recombinant vector can be prepared from an adenovirus vector having the E1-deleted region and having part of the adenovirus type 35 genome or an adenovirus vector having the E1-deleted region and having the entire adenovirus type 35 genome.

When preparing the recombinant adenovirus vector according to the present invention with the utilization of an adenovirus vector having the E1-deleted region and having part of the adenovirus type 35 genome, a foreign nucleotide sequence is first inserted into the E1-deleted region of the adenovirus vector, the resultant is ligated to the remaining portion of the adenovirus type 35 genome, and the ligation product is transfected into E1 protein- and E4 protein-expressing 293-cell, followed by recovery from the cells. Thus, the aforementioned recombinant adenovirus vector having a foreign nucleotide sequence can be prepared. In the case of an adenovirus vector consisting of the entire adenovirus type 35 genome having the E1-deleted region, a foreign nucleotide sequence can be inserted into the E1-deleted region to prepare the recombinant adenovirus vector having the aforementioned nucleotide sequence.

In general, when the E1 region is deleted from adenovirus, it cannot be proliferated in cells other than the E1 gene protein-expressing cell (for example, those of the 293-cell). For example, the E1 region-deleted adenovirus type 5 that is used as a vector for gene transfection can proliferate in cells of the 293-cell line, although it cannot proliferate in the target cell of gene transfection.

When the E1 region is deleted from adenovirus type 35, the adenovirus can proliferate in adenovirus type 5 E1 and E4 protein-expressing cells. However, the adenovirus cannot proliferate in cells in which the E1 protein is expressed but the E4 protein is not expressed. Specifically, proliferation characteristics of the E1 region-deleted adenovirus type 5 are different from those of the E1 region-deleted adenovirus type 35.

A foreign nucleotide sequence to be inserted into the E1-deleted region is not particularly limited, and any nucleotide sequence may be employed. Examples thereof include a nucleotide sequence that encodes a protein or peptide, a nucleotide sequence that is present in the regulatory region of a given gene, and a nucleotide sequence to which a given protein can bind. Particularly preferably, a gene that is effective or supposed to be effective for what is termed "gene therapy" is used as a foreign nucleotide sequence. More preferably, gene therapy includes treatment or prevention of diseases relating to hematopoietic cells, ES cells, pluripotent stem cells, blood stem cells, or tissue stem cells and gene therapy aimed at ameliorating symptoms caused by hematopoietic cells, ES cells, pluripotent stem cells, blood stem cells, or tissue stem cells.

When a nucleotide sequence having a promoter sequence that regulates gene expression, a gene that encodes luciferase, and a poly A sequence, in that order, is employed as a foreign nucleotide sequence, gene transfection efficiency to the target cell can be evaluated by assaying luciferase activity. When a gene that encodes a green fluorescent protein (so-called GFP) is used instead of the gene that encodes luciferase, gene transfection efficiency to the target cell can be evaluated by assaying the green fluorescence level in the target cell.

Preferably, hematopoietic cells such as CD34$^+$ cells or hematopoietic stem cells are used as the target cells of gene transfection. A receptor of the hematopoietic cell for adenovirus type 35 infection is unknown. A recombinant adenovirus vector having a foreign nucleotide sequence of luciferase, GFP, or another gene can assay the amount of foreign nucleotide sequence introduced. Thus, it is useful when searching for a receptor for infection in hematopoietic cells. Examples of the target cell for gene transfection that can be employed include ES cells, pluripotent stem cells, blood stem cells, and tissue stem cells.

It is known that adenovirus type 35 is highly compatible with human CD34$^+$ cells and that a chimera vector (Ad5/F35) comprising part of a fiber region of adenovirus type 35 in the capsid of adenovirus type 5 efficiently transfects genes to human CD34$^+$ cells (Shayakhmetov, D. M., Papayannopoulou, T., Stamatoyannopoulos, G. and Lieber, A., 2000, Efficient gene transfer into human CD34$^{(+)}$ cells by a retargeted adenovirus vector, J. Virol. 74, 2567-2583).

The recombinant adenovirus vector according to the present invention can also infect hematopoietic cells such as human CD34$^+$ cells with high compatibility. Furthermore, the recombinant adenovirus vector according to the present invention can efficiently introduce a nucleotide sequence that encodes a foreign peptide to hematopoietic cells.

The recombinant adenovirus vector according to the present invention is useful for repeated administration. When a common adenovirus type 5 vector is used for repeated administration to a subject animal, it is known that gene transfection efficiency is lowered as the number of administrations is increased as a result of an antigen-antibody reaction within the subject animal.

Accordingly, genes can be transfected into the subject animal with excellent efficiency at the second or later administration by, for example, conducting the first administration to the subject animal using a common adenovirus type 5 vector and then conducting the second or subsequent administrations to the subject animals using the recombinant adenovirus vector according to the present invention.

This description includes part or all of the contents as disclosed in the description and/or drawings of Japanese Patent Application No. 2002-164015, which is a priority document of the present application.

PREFERRED EMBODIMENTS OF THE INVENTION

The present invention is hereafter described in more detail with reference to the following examples, although the technical scope of the present invention is not limited thereto.

Example 1

Preparation of Adenovirus Type 35 Vector

Preparation of Plasmid

Figure 1:
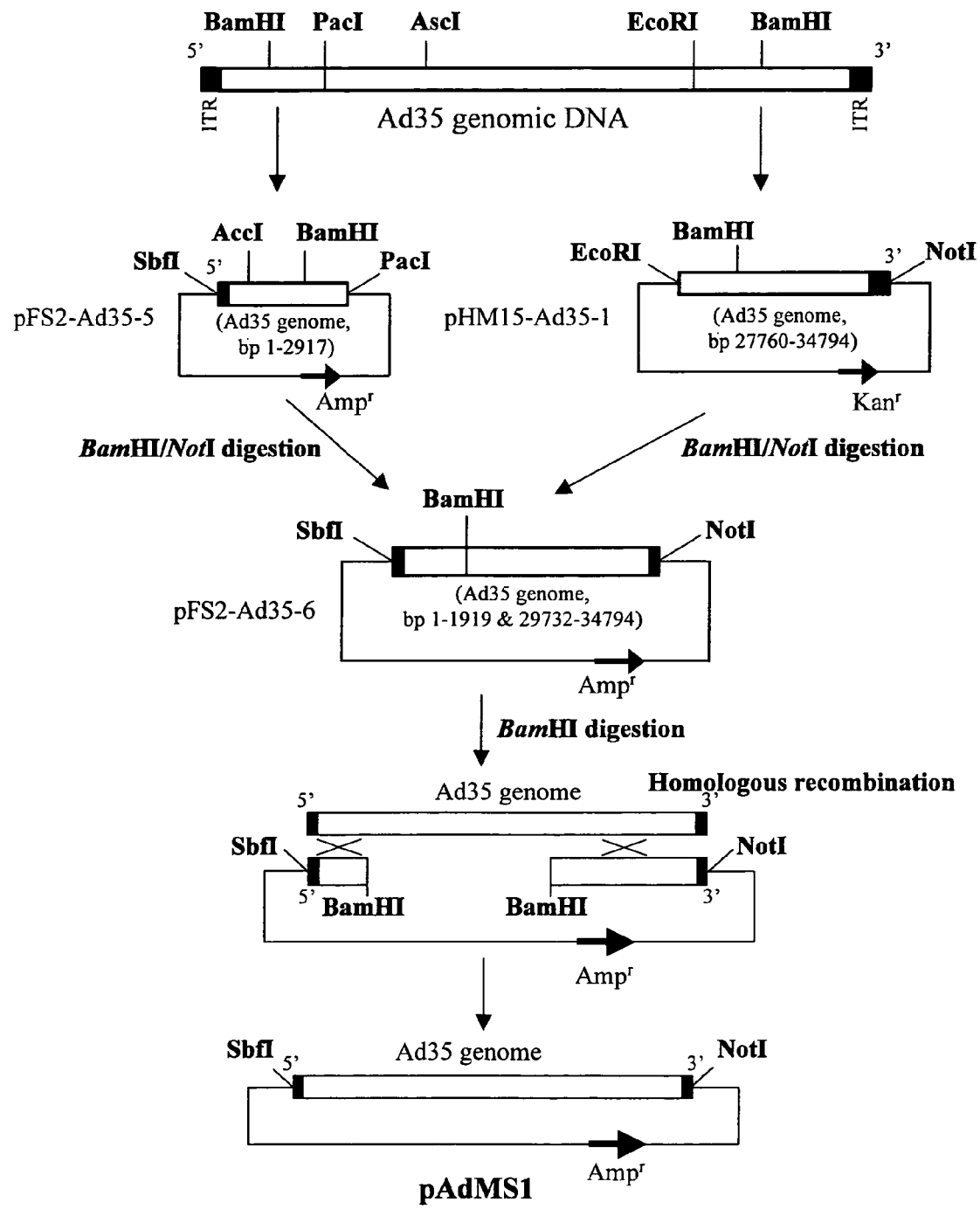
FIG. 1 shows a process of constructing a plasmid pAdMS1 having the adenovirus type 35 genome.

A plasmid (pAdMS1) having the SbfI recognition sequence and the NotI recognition sequence at the both terminuses of the adenovirus type 35 genome was first prepared. FIG. 1 shows the preparation procedure thereof.

When preparing pAdMS1, adenovirus type 35 (ATCC No. VR-718) was first obtained from the American Type Culture Collection (ATCC). The thus obtained adenovirus type 35 was proliferated in HeLa cells and purified via CsCl density gradient centrifugation. Adenovirus type 35 was then processed with proteinase K, thereby isolating adenovirus type 35 genomic DNA. An SbfI site was next added to the 5' terminus of the isolated genomic DNA. The genomic DNA was processed with PacI and the resulting 2,917 b fragment was cloned into the SbfI/PacI site of a pFS2 vector. The pFS2 vector having the 2,917 b fragment cloned therein was designated as pFS2-Ad35-5. The cloned 2,917 b fragment contained the 5' inverted terminal repetition (ITR) of adenovirus type 35. Further, a NotI site was added to the 3' terminus of the isolated genomic DNA. The genomic DNA was then processed with EcoRI. The resulting 7,034 b fragment was cloned into the EcoRI/NotI site of a pHM15 vector. The pHM15 vector having the 7,034 b fragment cloned therein was designated as pHM15-Ad35-1. The cloned fragment (approximately 7 kb) contained the 3' ITR of the adenovirus type 35 genome.

The pFS2 vector used herein was prepared by replacing the XbaI/XhoI/EcoRI/KpnI/SmaI/Csp45I/ClaI/HindIII/ BamHI/SacI site of pGEM7Zf (+) (Promega) with the SbfI/SwaI/PacI/AscI/SgfI/NotI site. The pHM15 vector was prepared by replacing the I-CeuI/HindIII/SphI site and the PI-SceI site of pHM5 (Mizuguchi, H. and Kay, M. A.: A simple method for constructing E1 and E1/E4 deleted recombinant adenovirus vector: Hum. Gene Ther., 10, 2013-2017, 1999) with the XbaI/AvrII/NheI/SpeI/NotI site and the PvuII/ApaI/SpeI/NheI/AvrII/XbaI site, respectively.

The thus obtained pFS2-Ad35-5 and pHM15-Ad35-1 were then digested with BamHI and NotI, respectively. Accordingly, pFS2-Ad35-5 was linearized by being cleaved at the BamHI recognition site in a region derived from genomic DNA. Separately, a BamHI-NotI fragment containing a region derived from the genomic DNA was cleaved out of pHM15-Ad35-1 in accordance with a conventional technique. The vector obtained by ligating the linearized pFS2-Ad35-5 fragment to the cleaved BamHI-NotI fragment was designated as pFS2-Ad35-6.

The obtained pFS2-Ad35-6 was linearized by digestion with BamHI. The linearized pFS2-Ad35-6 and adenovirus type 35 genomic DNA were transformed into an *E. coli* BJ5183 strain. Thus, homologous recombination took place between pFS2-Ad35-6 and adenovirus type 35 genomic DNA in the *E. coli* BJ5183 strain. Subsequently, a plasmid pAdMS1 was prepared by extracting a plasmid from the *E. coli* BJ5183 strain in accordance with a conventional technique.

Figure 2:
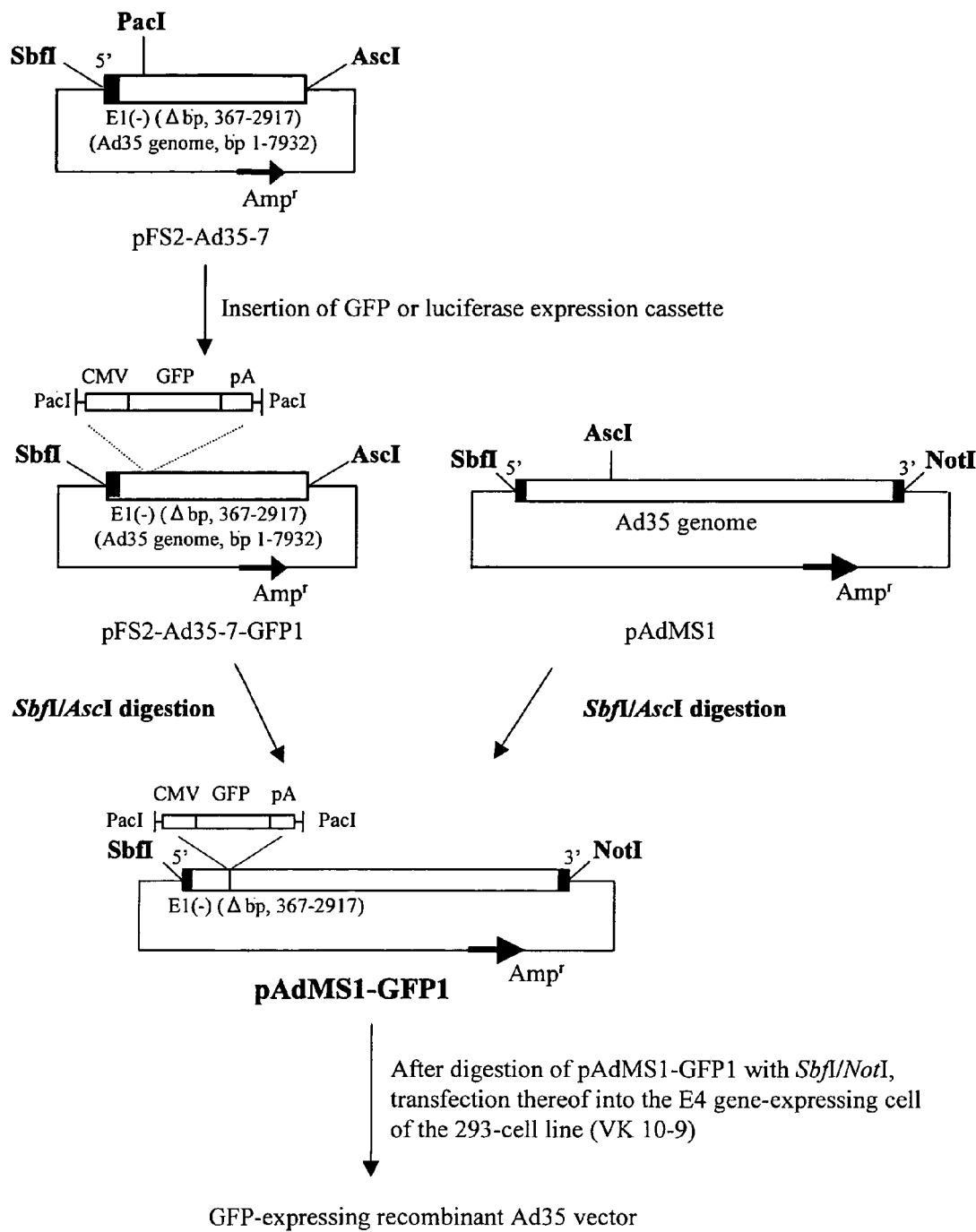
FIG. 2 shows a process of constructing Ad35GFP having a GFP expression cassette.

A GFP-expressing recombinant adenovirus vector was prepared using a plasmid pAdMS1. FIG. 2 shows the preparation procedure thereof First, adenovirus type 35 genomic DNA was digested with PacI and AscI, thereby cleaving out a PacI/AscI fragment equivalent to the region between nucleotides 2,917 to 7,932 of the aforementioned genomic DNA. Secondly, pFS2-Ad35-5 was digested with AccI and PacI, thereby removing an AccI/PacI fragment equivalent to the region between nucleotides 367 to 2,917 of adenovirus type 35 genomic DNA and converting an AccI recognition site into a PacI recognition site. The resultant was further digested with PacI and AscI and ligated to a PacI/AscI fragment equivalent to the region between nucleotides 2,917 to 7,932 of adenovirus type 35 genomic DNA. This enabled construction of a plasmid consisting of a nucleotide sequence derived from the nucleotide sequence consisting of nucleotides 1 to 7,932 of the genomic DNA by deletion of nucleotides 367 to 2,917 and conversion of the AccI recognition site into the PacI recognition site. The thus obtained plasmid was designated as pFS2-Ad35-7.

Next, a GFP expression cassette in which the cytomegarovirus (CMV) promoter, the GFP gene, and the bovine growth hormone (BGH) poly A sequence were ligated in that order were integrated and then cloned into the PacI recognition site of pFS2-Ad35-7. The resulting plasmid was designated as pFS2-Ad35-7-GFP1. The pFS2-Ad35-7-GFP1 and pAdMS1 (FIG. 1) were digested with SbfI and AscI, respectively. A fragment containing a GFP expression cassette of pFS2-Ad35-7-GFP1 was ligated to a fragment prepared by removing an SbfI/AscI fragment (equivalent to the region between nucleotides 1 to 7,932 of the genomic DNA) from a plasmid pAdMS1. As a result, a plasmid pAdMS1-GFP1 that contains adenovirus type 35 genomic DNA having a GFP expression cassette incorporated in the E1-deleted region was constructed.

Also, a plasmid pAdMS1-L2 that contains adenovirus type 35 genomic DNA having a luciferase expression cassette incorporated in the E1-deleted region was constructed in a manner similar to that used for pAdMS1-GFP1.

Construction of Recombinant Adenovirus Vector

The thus obtained pAdMS1-GFP1 and pAdMS1-L2 were constructed as recombinant adenovirus vectors in the following manner. That is, pAdMS1-GFP1 and pAdMS1-L2 were first digested with SbfI and NotI, respectively, and then transfected into the 293-cell line (VK10-9), which simultaneously expresses the E1 and E4 genes. Cytopathic effects were observed 10 to 14 days after the transfection, and amplification of the viruses derived from the plasmids was confirmed. The viruses derived from the plasmids were purified in accordance with a conventional technique (Lieber, A. et al., J. Virol. 70, 8944-8960, 1996).

As a result, the yield of the virus derived from pAdMS1-GFP1 (Ad35GFP) was approximately 1.5 ml at cell densities of $10^{11}$ virus particles/ml. This yield was substantially equivalent to or somewhat smaller than that of adenovirus type 5. The virus derived from pAdMS1-L2 (Ad35L) was purified in the same manner as described above. Thus, the adenovirus type 35 vector having a GFP expression cassette incorporated therein and the adenovirus type 35 vector having a luciferase expression cassette incorporated therein were constructed.

As the control, vectors having a GFP expression cassette or a luciferase expression cassette incorporated therein, Ad5GFP and Ad5F35GFP, were constructed using a normal adenovirus type 5 vector (Ad5) and the adenovirus type 5 vector (Ad5F35), the fiber region of which had been substituted with that of adenovirus type 35.

The ratio of the plaque forming unit (PFU) to the virus particle titer was 1:133 for Ad35GFP, 1:24 for Ad5F35GFP, 1:56 for Ad5GFP, 1:225 for Ad35L, 1:13 for Ad5F3 5L, and 1:13 for Ad5L. The PFU was measured in accordance with the method disclosed in Kanegae Y. et al., Jpn. J. Med. Sci. Biol., 1994, 47: 157-166. The virus particle titer was measured in accordance with the method disclosed in Maizel Jv. et. al., Virology. 1968, 36: 115-125.

Experimentation of Gene Transfection into Hematocytes

Gene transfection into hematocytes was carried out using the recombinant adenovirus vectors (Ad35GFP and Ad35L) constructed above. Human CD34$^+$ cells (BioWhittaker) were employed as hematocytes. According to the manufacturer's instructions, 95% or more of the cells were CD34 positive.

16 to 20 hours before the initiation of the gene transfection experiment, human CD34$^+$ cells were converted from a cryopreserved state, and then were dissolved in StemSpan™ 2000 (StemCell Technologies, Inc). The StemSpan™ 2000 was used for the experiment in the form of a mixture with cytokine cocktail StemSpan™ CC100 (human flt-3 ligand (100 ng/ml), human stem cell factor (100 ng/ml), human interleukin-3 (20 ng/ml), and human interleukin-6 (20 ng/ml)). Thereafter, human CD34$^+$ cells were inoculated on a 24-well plate at a cell density of $1\times10^5$ cells/well. Ad35GFP, Ad5GFP, and Ad5F35GFP were diluted to cell densities of 3 PFU/cell, 30 PFU/cell, and 300 PFU/cell, respectively. Gene transfection into human CD34+ cells was carried out employing Ad35GFP, Ad5GFP, and Ad5F35GFP at the aforementioned densities, respectively.

48 hours thereafter, expression of the GFP gene in human CD34+ cells was analyzed by flow cytometry using a FACScalibur flow cytometer equipped with the CellQuest software (Becton Dickinson). The results are shown in FIG. 3.

Figure 4:
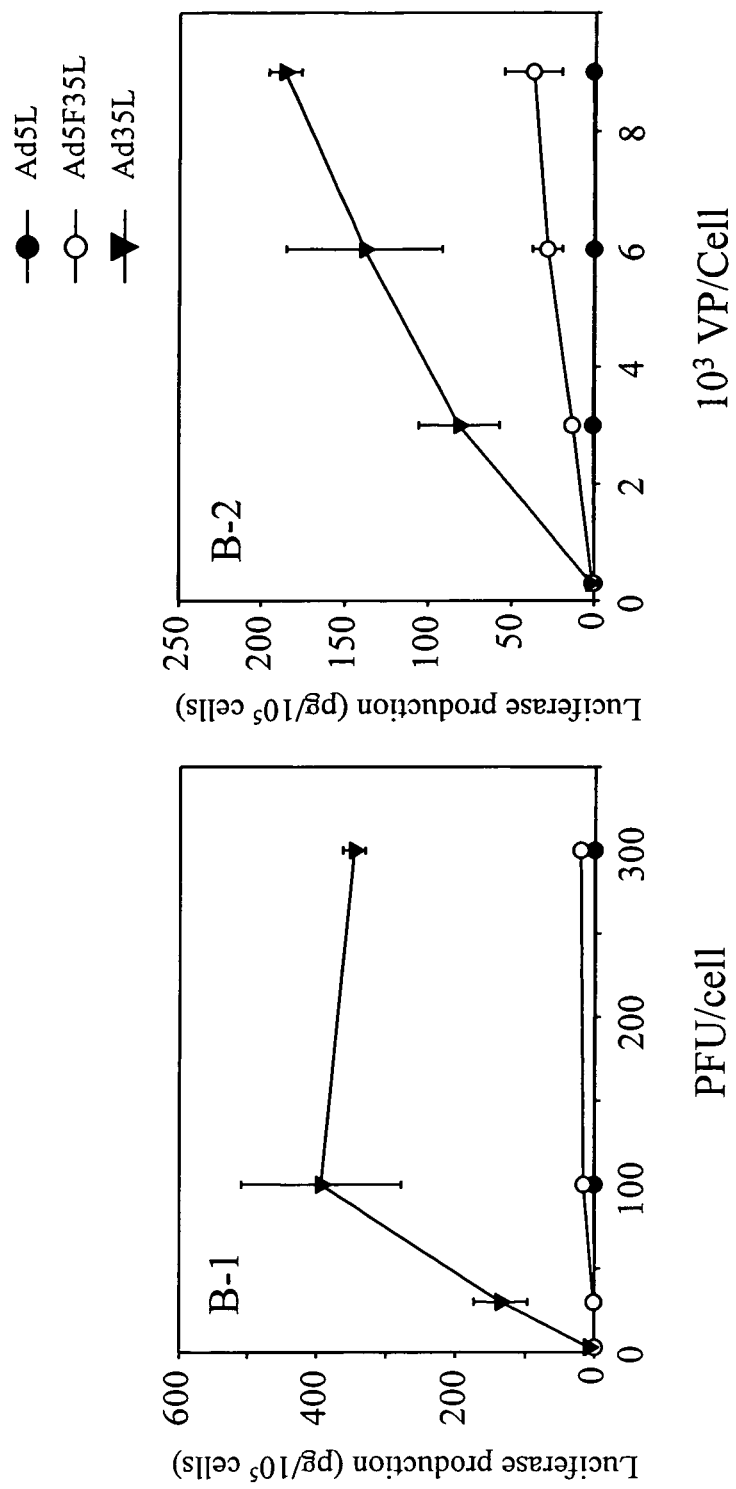
FIG. 4 is a cause-and-effect diagram showing luciferase activities assayed as a result of gene transfection using Ad5L, Ad5F35L, and Ad35L.

When Ad35L, Ad5L, and Ad5F35L were used, human CD34+ cells were inoculated on a 96-well plate at a cell density of $1\times10^4$ cells/well. Ad35L, Ad5L, and Ad5F35L were diluted to cell densities of 3, 30, 100, and 300 PFU/cell and to cell densities of 300, 3,000, 6,000, and 9,000 vector particles/cell, respectively. Gene transfection into human CD34+ cells was carried out employing Ad35L, Ad5L, and Ad5F35L at the aforementioned densities, respectively. 48 hours thereafter, luciferase gene expression in human CD34+ cells was evaluated using the luciferase assay system (PicaGene LT 2.0, Toyo Ink). The results are shown in FIG. 4. In FIG. 4, "B-1" shows the results attained when the viruses were used at cell densities of 3, 30, 100, and 300 PFU/cell, respectively, and "B-2" shows the results attained when the viruses were used at cell densities of 300, 3,000, 6,000, and 9,000 vector particles/cell, respectively.

Evaluation of Gene Transfection into Hematocytes Using Each Virus

Figure 3:
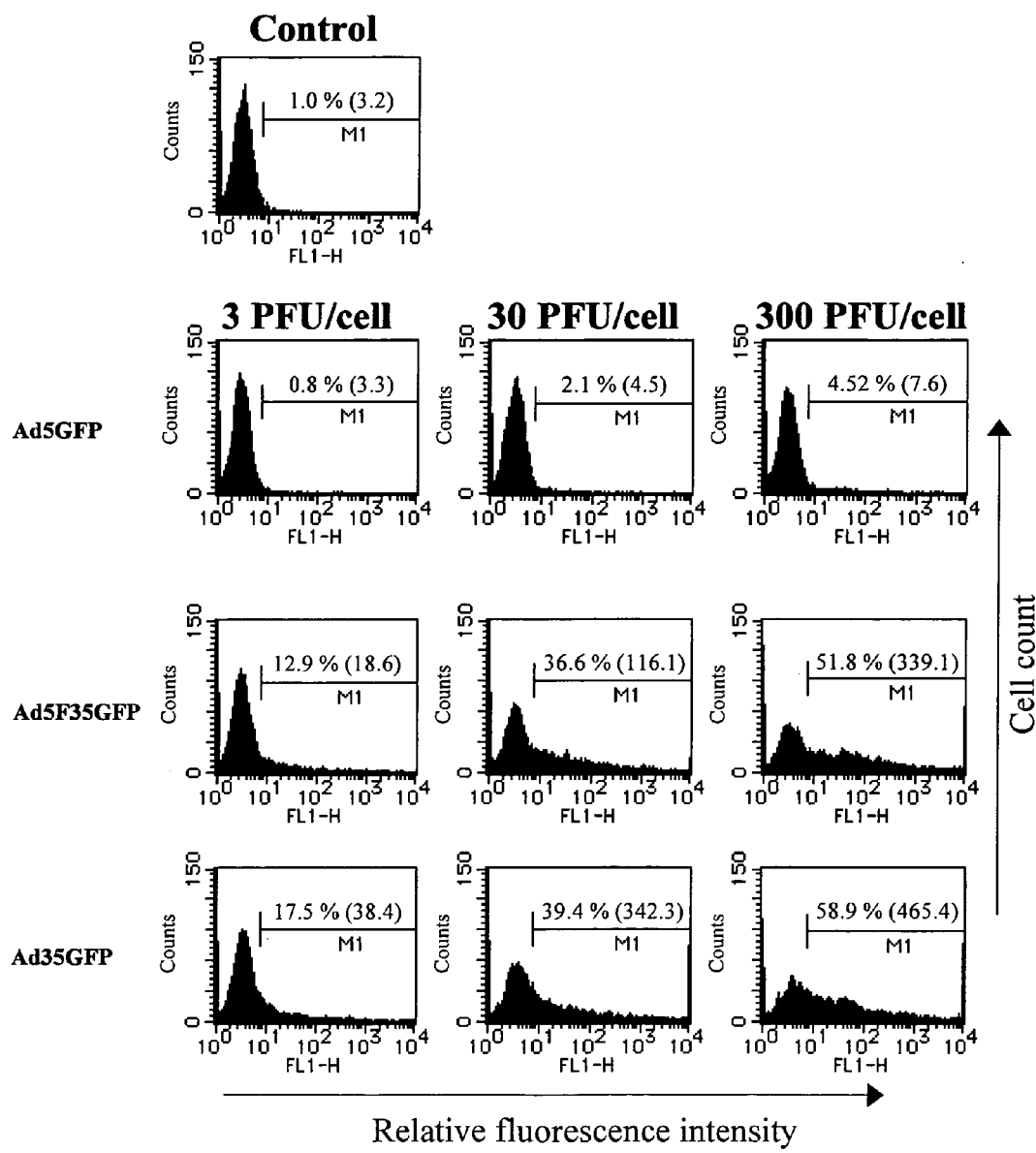
FIG. 3 is a cause-and-effect diagram showing fluorescence intensities assayed as a result of gene transfection using Ad5GFP, Ad5F35GFP, and Ad35GFP.

The results shown in FIG. 3 show that the use of Ad35GFP can result in GFP gene transfection with much higher efficiency than the use of Ad5GFP and Ad5F35GFP. Particularly when Ad35GFP was used at a cell density of 300 PFU/cell, the GFP gene was expressed in 59% of human CD34+ cells. At the same density, the GFP gene was expressed in 5% and 52% of human CD34+ cells with the use of Ad5GFP and Ad5F35GFP, respectively. The mean fluorescence intensity (MFI) with the use of Ad35GFP was 10 to 70 times larger than that with the use of Ad5GFP, and 2 to 3 times larger than that with the use of Ad5F35GFP.

The results shown in "B-1" of FIG. 4 indicate that the level of luciferase expression with the use of Ad35L was 1,000 to 3,000 times larger than that with the use of Ad5L and 15 to 100 times larger than that with the use of Ad5F35L. Unlike the case of adenovirus type 5, the 293-cell line expressing the E4 gene product may not completely produce adenovirus type 35. Thus, there is a possibility that gene transfection efficiency measured with the PFU titer may be underestimated for Ad35L as shown in "B-1" of FIG. 4. Therefore, gene transfection efficiency was evaluated at cell densities of 300, 3,000, 6,000, and 9,000 vector particles/cell. As a result, gene transfection efficiency of Ad35L was found to be higher than that of Ad5L and that of Ad5F35L at a cell density of 3,000 vector particles/cell or higher, as shown in "B-2" of FIG. 4.

Accordingly, gene transfection efficiency into human CD34+ cells was much better when Ad35 was used than when Ad5 or Ad5F35 was used. Thus, gene transfection using Ad35 was found to be particularly effective on hematocytes such as hematopoietic stem cells.

Repeated In Vivo Administration Experiment Using Ad35

In this embodiment, the usefulness of Ad35 was examined by a repeated in vivo administration experiment consisting of a first administration with the use of Ad5 and a subsequent second administration with the use of Ad35 for gene transfection.

Mice (C57Bl6, Japan SLC) were used as experimental animals. In addition, Ad5L was employed for the first administration. Ad35 (Ad35RSVSEAP1) having a human secretory enzymatic alkaline phosphatase (SEAP) expression cassette (RSVSEAP1) incorporated therein was used for the second administration in accordance with the method described above. In RSVSEAP1, the Rous sarcoma virus (RSV) promoter, the SEAP gene, and the BGH poly A sequence were ligated in that order. As the control, Ad5 (Ad5RSVSEAP1) having RSVSEAP1 incorporated therein was used for the second administration. The repeated in vivo administration experiment was conducted according to the following procedure.

Ad5L was first administered to the caudal veins of mice in amounts of $1.5\times10^{10}$ vector particles/mouse. 14 days after the first administration, Ad5RSVSEAP1 or Ad35RSVSEAP1 was administered intramuscularly to the mice in amounts of $1.5\times10^{10}$ vector particles/mouse. Blood was sampled from the ophthalmic vessels of mice 2 days after the second administration to measure the amount of serum SEAP. The amount of SEAP was measured using the Great EscAPe™ SEAP Chemiluminescence Detection Kit (Clontech). Ad5RSVSEAP1 or Ad35RSVSEAP1 was administered intramuscularly to the control group via the second administration while no first administration took place.

Figure 5:
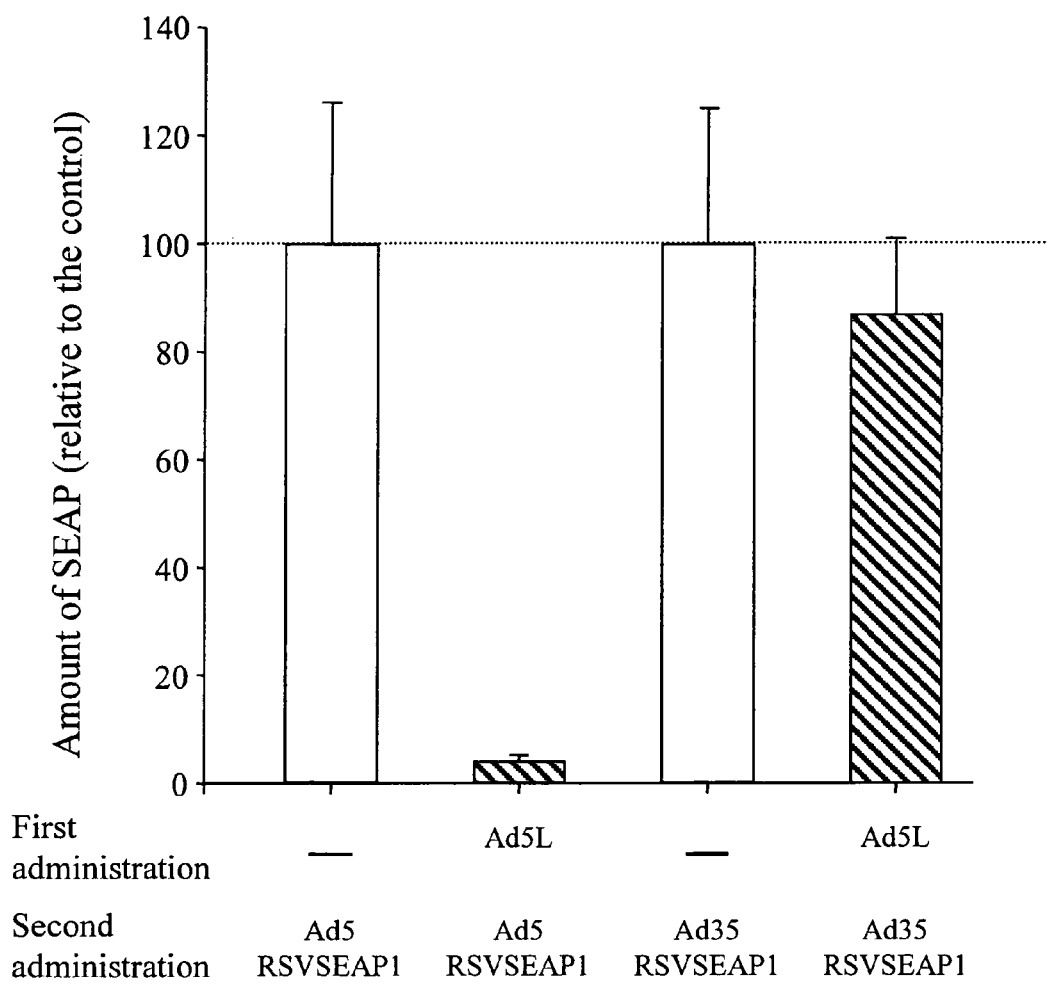
FIG. 5 is a cause-and-effect diagram showing the results of the repeated in vivo administration experiment using Ad35.

The results are shown in FIG. 5. The data in FIG. 5 are shown in terms of the mean value of four experimental measures±S.D. The vertical axis represents the amount of SEAP, which is a relative value attained when the SEAP amount of the control group is determined to be 100%. When Ad5 was used for the first and second administrations, the amount of SEAP resulting from the second administration fell to 5% or less that of the group to which no first administration had been made (the control group). In contrast, when Ad5 was used in the first administration and Ad35 was used in the second administration, the amount of SEAP resulting from the second administration was almost equal to that of the group to which no first administration had been made (the control group).

As described above, employment of commonly used adenovirus vectors, such as Ad5 for the first administration and Ad35 for the second or subsequent administrations, can prevent a disadvantage whereby the gene transfection efficiency is lowered as the number of administration is increased. Thus, it has been proved that gene transfection can be carried out with excellent efficiency at the second or subsequent administration.

All publications, patents, and patent applications cited herein are incorporated herein by reference in their entirety.

INDUSTRIAL APPLICABILITY

As is apparent from the foregoing detailed description, the present invention can provide an adenovirus vector that has excellent gene transfection efficiency on specific cell lines, particularly on hematopoietic cells, a method for producing such vector, and a method for gene transfection using such vector.

The invention claimed is:

1. An adenovirus type 35 vector, comprising an adenovirus type 35 genome from which there are deleted (A) a segment of the E1 region, wherein the segment consists of nucleotides 367 to 2,917 and (B) a segment of the E3 region, wherein the segment consists of nucleotides 27,760 to 29,732.

2. The adenovirus type 35 vector according to claim 1, wherein a foreign gene is inserted into the deleted E1 or the deleted E3 region.

3. A method for gene transfection, comprising providing the adenovirus type 35 vector according to claim 1 and infecting a target cell, wherein the vector comprises a foreign gene.

4. The method for gene transfection according to claim 3, wherein the target cell is selected from the group consisting of hematopoietic cells, blood stem cells, ES cells, pluripotent stem cells, and tissue stem cells.

5. The method for gene transfection according to claim 3, wherein the target cell is a CD34+ cell.

* * * * *